(12) United States Patent
Ignon et al.

(10) Patent No.: US 9,486,615 B2
(45) Date of Patent: *Nov. 8, 2016

(54) MICRODERMABRASION APPARATUS AND METHOD

(75) Inventors: Roger Ignon, Redondo Beach, CA (US); Ed F. Nicolas, Wilmington, CA (US)

(73) Assignee: Edge Systems LLC, Signal Hill, CA (US)

( * ) Notice: Subject to any disclaimer, the term of this patent is extended or adjusted under 35 U.S.C. 154(b) by 595 days.

This patent is subject to a terminal disclaimer.

(21) Appl. No.: 13/620,376

(22) Filed: Sep. 14, 2012

(65) Prior Publication Data

US 2013/0102978 A1    Apr. 25, 2013

Related U.S. Application Data

(63) Continuation of application No. 12/346,582, filed on Dec. 30, 2008, now Pat. No. 8,343,116.

(60) Provisional application No. 61/019,196, filed on Jan. 4, 2008, provisional application No. 61/022,201, filed on Jan. 18, 2008.

(51) Int. Cl.
*A61M 35/00* (2006.01)
*A61B 17/3205* (2006.01)

(52) U.S. Cl.
CPC .................................. *A61M 35/003* (2013.01)

(58) Field of Classification Search
USPC ...................................................... 606/9, 131
See application file for complete search history.

(56) References Cited

U.S. PATENT DOCUMENTS

| | | | |
|---|---|---|---|
| 2,608,032 A | 8/1952 | Garver | |
| 2,631,583 A * | 3/1953 | Lavergne | A61H 9/005 15/321 |
| 2,701,559 A | 2/1955 | Cooper | |
| 2,712,823 A | 7/1955 | Kurtin | |
| 2,867,214 A | 1/1959 | Wilson | |
| 2,881,763 A | 4/1959 | Robbins | |
| 2,921,585 A | 1/1960 | Schumann | |
| 3,085,573 A | 4/1963 | Meyer et al. | |
| 3,214,869 A | 11/1965 | Stryker | |
| 3,476,112 A | 11/1969 | Elstein | |

(Continued)

FOREIGN PATENT DOCUMENTS

| | | |
|---|---|---|
| DE | 34 21 390 A1 | 12/1985 |
| DE | 234 608 | 4/1986 |

(Continued)

OTHER PUBLICATIONS

International Search Report for PCT/US2008/088576 (the corresponding PCT of the subject application), mailed Feb. 19, 2009.

(Continued)

*Primary Examiner* — Paula L. Craig
(74) *Attorney, Agent, or Firm* — Knobbe, Martens, Olson & Bear, LLP

(57) ABSTRACT

According to some embodiments, a system for treating skin includes a handpiece assembly comprising a tip and a main body portion, the main body portion comprising an interior cavity and at least one canister configured to store at least one of a treatment material and a waste material. The treatment material and/or the waste material is in fluid communication with the tip.

20 Claims, 17 Drawing Sheets

(56) References Cited

U.S. PATENT DOCUMENTS

| | | | |
|---|---|---|---|
| 3,574,239 A * | 4/1971 | Sollerud | 4/616 |
| 3,715,838 A | 2/1973 | Young et al. | |
| 3,865,352 A | 2/1975 | Nelson et al. | |
| 3,948,265 A | 4/1976 | Al Ani | |
| 3,964,212 A | 6/1976 | Karden | |
| 3,977,084 A | 8/1976 | Sloan | |
| 4,121,388 A | 10/1978 | Wilson | |
| 4,155,721 A | 5/1979 | Fletcher | |
| 4,170,821 A * | 10/1979 | Booth | B05D 5/08 30/41 |
| 4,182,329 A | 1/1980 | Smit et al. | |
| 4,203,431 A | 5/1980 | Abura et al. | |
| 4,216,233 A | 8/1980 | Stein | |
| 4,299,219 A | 11/1981 | Norris, Jr. | |
| 4,378,804 A | 4/1983 | Cortese | |
| 4,560,373 A | 12/1985 | Sugino et al. | |
| 4,646,480 A | 3/1987 | Williams | |
| 4,646,482 A | 3/1987 | Chitjian | |
| 4,655,743 A | 4/1987 | Hyde | |
| 4,676,749 A | 6/1987 | Mabille | |
| 4,706,676 A | 11/1987 | Peck | |
| 4,754,756 A | 7/1988 | Shelanski | |
| 4,757,814 A | 7/1988 | Wang et al. | |
| 4,764,362 A | 8/1988 | Barchas | |
| 4,795,421 A | 1/1989 | Blasius, Jr. et al. | |
| 4,875,287 A | 10/1989 | Creasy et al. | |
| 4,886,078 A | 12/1989 | Shiffman | |
| 4,887,994 A | 12/1989 | Bedford | |
| 4,900,316 A | 2/1990 | Yamamoto | |
| 4,917,086 A | 4/1990 | Feltovich et al. | |
| 4,925,450 A | 5/1990 | Imonti et al. | |
| 4,957,747 A | 9/1990 | Stiefel | |
| 5,006,004 A | 4/1991 | Dirksing et al. | |
| 5,006,339 A | 4/1991 | Bargery et al. | |
| 5,012,797 A | 5/1991 | Liang et al. | |
| 5,035,089 A | 7/1991 | Tillman et al. | |
| 5,037,431 A | 8/1991 | Summers et al. | |
| 5,037,432 A * | 8/1991 | Molinari | 606/131 |
| 5,100,412 A | 3/1992 | Rosso | |
| 5,100,424 A | 3/1992 | Jang et al. | |
| 5,119,839 A | 6/1992 | Rudolph | |
| 5,122,153 A | 6/1992 | Harrel | |
| 5,207,234 A | 5/1993 | Rosso | |
| 5,222,956 A | 6/1993 | Waldron | |
| 5,242,433 A | 9/1993 | Smith et al. | |
| 5,254,109 A | 10/1993 | Smith et al. | |
| 5,368,581 A | 11/1994 | Smith et al. | |
| 5,391,151 A | 2/1995 | Wilmot | |
| 5,417,674 A | 5/1995 | Smith et al. | |
| 5,419,772 A | 5/1995 | Teitz et al. | |
| 5,460,620 A | 10/1995 | Smith et al. | |
| 5,470,323 A | 11/1995 | Smith et al. | |
| 5,484,427 A | 1/1996 | Gibbons | |
| 5,562,642 A | 10/1996 | Smith et al. | |
| 5,611,687 A | 3/1997 | Wagner | |
| 5,612,797 A | 3/1997 | Liang et al. | |
| 5,674,235 A | 10/1997 | Parisi | |
| 5,676,643 A | 10/1997 | Cann et al. | |
| 5,676,648 A | 10/1997 | Henley | |
| 5,683,971 A | 11/1997 | Rose et al. | |
| 5,697,920 A * | 12/1997 | Gibbons | 604/289 |
| 5,707,383 A | 1/1998 | Bays | |
| 5,713,785 A | 2/1998 | Nishio | |
| 5,735,833 A * | 4/1998 | Olson | 604/289 |
| 5,759,185 A | 6/1998 | Grinberg | |
| 5,779,519 A | 7/1998 | Oliver | |
| 5,800,446 A | 9/1998 | Banuchi | |
| 5,807,353 A | 9/1998 | Schmitz | |
| 5,810,842 A | 9/1998 | Di Fiore et al. | |
| 5,813,416 A | 9/1998 | Rudolph | |
| 5,817,050 A | 10/1998 | Klein | |
| 5,846,215 A | 12/1998 | Zygmont | |
| 5,848,998 A | 12/1998 | Marasco, Jr. | |
| 5,861,142 A | 1/1999 | Schick | |
| 5,873,881 A | 2/1999 | McEwen et al. | |
| 5,879,323 A | 3/1999 | Henley | |
| 5,882,201 A | 3/1999 | Salem | |
| 5,885,260 A | 3/1999 | Mehl, Sr. et al. | |
| 5,908,401 A | 6/1999 | Henley | |
| 5,919,152 A | 7/1999 | Zygmont | |
| 5,954,730 A | 9/1999 | Bernabei | |
| 5,971,999 A | 10/1999 | Naldoni | |
| 5,980,555 A | 11/1999 | Barbut et al. | |
| 6,019,749 A | 2/2000 | Fields et al. | |
| 6,024,733 A | 2/2000 | Eggers et al. | |
| 6,027,402 A | 2/2000 | Oliver | |
| 6,039,745 A | 3/2000 | Di Fiore et al. | |
| 6,042,552 A | 3/2000 | Cornier | |
| 6,080,165 A * | 6/2000 | DeJacma | 606/131 |
| 6,080,166 A | 6/2000 | McEwen et al. | |
| 6,090,085 A | 7/2000 | Mehl, Sr. et al. | |
| 6,120,512 A | 9/2000 | Bernabei | |
| 6,129,701 A | 10/2000 | Cimino | |
| 6,136,008 A | 10/2000 | Becker et al. | |
| 6,139,553 A | 10/2000 | Dotan | |
| 6,139,554 A | 10/2000 | Karkar et al. | |
| 6,142,155 A | 11/2000 | Rudolph | |
| 6,149,634 A | 11/2000 | Bernabei | |
| 6,159,226 A | 12/2000 | Kim | |
| 6,162,218 A * | 12/2000 | Elbrecht et al. | 606/41 |
| 6,162,232 A * | 12/2000 | Shadduck | 606/131 |
| 6,183,451 B1 | 2/2001 | Mehl, Sr. et al. | |
| 6,183,483 B1 | 2/2001 | Chang | |
| 6,193,589 B1 | 2/2001 | Khalaj | |
| 6,231,593 B1 | 5/2001 | Meserol | |
| 6,235,039 B1 * | 5/2001 | Parkin et al. | 606/131 |
| 6,238,275 B1 | 5/2001 | Metcalf et al. | |
| 6,241,739 B1 | 6/2001 | Waldron | |
| 6,264,666 B1 | 7/2001 | Coleman et al. | |
| 6,277,128 B1 | 8/2001 | Muldner | |
| 6,283,978 B1 | 9/2001 | Cheski et al. | |
| 6,299,620 B1 * | 10/2001 | Shadduck et al. | 606/131 |
| 6,306,119 B1 | 10/2001 | Weber et al. | |
| 6,306,147 B1 | 10/2001 | Bernabei et al. | |
| 6,322,568 B1 | 11/2001 | Bernabei et al. | |
| 6,368,333 B2 * | 4/2002 | Bernabei et al. | 606/131 |
| 6,387,103 B2 | 5/2002 | Shadduck | |
| 6,409,736 B1 | 6/2002 | Bernabei | |
| 6,410,599 B1 | 6/2002 | Johnson | |
| RE37,796 E | 7/2002 | Henley | |
| 6,414,032 B1 | 7/2002 | Johnson | |
| 6,420,431 B1 | 7/2002 | Johnson | |
| 6,423,078 B1 | 7/2002 | Bays et al. | |
| 6,423,750 B1 | 7/2002 | Johnson | |
| 6,432,113 B1 | 8/2002 | Parkin et al. | |
| 6,432,114 B1 | 8/2002 | Rosso | |
| 6,471,712 B2 | 10/2002 | Burres | |
| 6,477,410 B1 | 11/2002 | Henley et al. | |
| 6,482,212 B1 | 11/2002 | Bernabei et al. | |
| 6,488,646 B1 | 12/2002 | Zygmont | |
| 6,494,856 B1 | 12/2002 | Zygmont | |
| 6,500,183 B1 * | 12/2002 | Waldron | 606/131 |
| 6,503,256 B2 | 1/2003 | Parkin et al. | |
| 6,511,486 B2 * | 1/2003 | Mercier et al. | 606/131 |
| 6,514,262 B1 | 2/2003 | Di Fiore et al. | |
| 6,527,783 B1 * | 3/2003 | Ignon | 606/131 |
| 6,535,761 B2 | 3/2003 | Bernabei | |
| 6,540,757 B1 * | 4/2003 | Hruska et al. | 606/131 |
| 6,562,013 B1 | 5/2003 | Marasco, Jr. | |
| 6,562,050 B1 | 5/2003 | Owen | |
| 6,564,093 B1 | 5/2003 | Ostrow et al. | |
| 6,565,535 B2 | 5/2003 | Zaias et al. | |
| 6,582,442 B2 | 6/2003 | Simon et al. | |
| 6,589,218 B2 * | 7/2003 | Garcia | 604/313 |
| 6,592,595 B1 | 7/2003 | Mallett et al. | |
| 6,629,983 B1 | 10/2003 | Ignon | |
| 6,641,591 B1 | 11/2003 | Shadduck | |
| 6,645,184 B1 | 11/2003 | Zelickson et al. | |
| 6,652,888 B2 | 11/2003 | Rhoades | |
| 6,673,081 B1 | 1/2004 | Tavger et al. | |
| 6,673,082 B2 | 1/2004 | Mallett et al. | |
| 6,685,853 B1 | 2/2004 | Angelopoulos et al. | |
| 6,687,537 B2 | 2/2004 | Bernabei | |
| 6,695,853 B2 | 2/2004 | Karasiuk | |

(56) References Cited

U.S. PATENT DOCUMENTS

| | | | |
|---|---|---|---|
| 6,735,470 B2 | 5/2004 | Henley et al. | |
| 6,743,211 B1 | 6/2004 | Prausnitz et al. | |
| 6,743,215 B2 | 6/2004 | Bernabei | |
| 6,764,493 B1 | 7/2004 | Weber et al. | |
| 6,869,611 B1 | 3/2005 | Kligman et al. | |
| 6,905,487 B2 | 6/2005 | Zimmerman | |
| 6,911,031 B2 | 6/2005 | Muldner | |
| 6,924,649 B2 | 8/2005 | Knoedgen | |
| 6,926,681 B1 | 8/2005 | Ramey et al. | |
| 6,942,649 B2 | 9/2005 | Ignon et al. | |
| 7,001,355 B2 | 2/2006 | Nunomura et al. | |
| 7,004,933 B2 | 2/2006 | McDaniel | |
| 7,044,938 B2 | 5/2006 | La Bianco et al. | |
| 7,052,503 B2 | 5/2006 | Bernabei | |
| 7,069,073 B2 | 6/2006 | Henley et al. | |
| 7,070,488 B2 | 7/2006 | Suissa et al. | |
| 7,083,580 B2 | 8/2006 | Bernabei | |
| 7,087,063 B2 | 8/2006 | Carson et al. | |
| 7,094,252 B2 | 8/2006 | Koop | |
| 7,115,275 B2 | 10/2006 | Clarot et al. | |
| 7,135,011 B2 | 11/2006 | Powers et al. | |
| 7,153,311 B2 | 12/2006 | Chung | |
| 7,197,359 B1 | 3/2007 | Tokudome et al. | |
| 7,198,623 B2 | 4/2007 | Fischer et al. | |
| 7,232,444 B2 | 6/2007 | Chang | |
| 7,241,208 B2 | 7/2007 | Suissa et al. | |
| 7,276,051 B1 | 10/2007 | Henley et al. | |
| 7,314,326 B2 | 1/2008 | Rosenberg | |
| 7,316,657 B2 | 1/2008 | Kleinhenz et al. | |
| 7,318,828 B1 | 1/2008 | Revivo | |
| 7,320,691 B2 | 1/2008 | Pilcher et al. | |
| 7,320,801 B2 | 1/2008 | Kelly | |
| 7,354,423 B2 | 4/2008 | Zelickson et al. | |
| 7,364,565 B2 | 4/2008 | Freeman | |
| 7,384,405 B2 | 6/2008 | Rhoades | |
| 7,427,273 B2 | 9/2008 | Mitsui | |
| 7,458,944 B2 | 12/2008 | Liste et al. | |
| 7,476,205 B2 | 1/2009 | Erdmann | |
| 7,477,938 B2 | 1/2009 | Sun et al. | |
| 7,482,314 B2 | 1/2009 | Grimes et al. | |
| 7,489,989 B2 | 2/2009 | Sukhanov et al. | |
| 7,507,228 B2 | 3/2009 | Sun et al. | |
| 7,582,067 B2 | 9/2009 | Van Acker | |
| 7,597,900 B2 | 10/2009 | Zimmer et al. | |
| 7,597,901 B2 | 10/2009 | Clarot et al. | |
| 7,658,742 B2 | 2/2010 | Karasiuk | |
| 7,678,120 B2 | 3/2010 | Shadduck | |
| 7,744,582 B2 | 6/2010 | Sadowski et al. | |
| 7,789,886 B2 | 9/2010 | Shadduck | |
| 7,837,695 B2 | 11/2010 | Hart et al. | |
| 7,901,373 B2 | 3/2011 | Tavger | |
| 7,951,156 B2 | 5/2011 | Karasiuk | |
| 8,025,669 B1 | 9/2011 | David et al. | |
| RE42,960 E | 11/2011 | Waldron | |
| 8,048,089 B2 | 11/2011 | Ignon et al. | |
| 8,066,716 B2 | 11/2011 | Shadduck | |
| 8,088,085 B2 | 1/2012 | Thiebaut et al. | |
| 8,128,638 B2 | 3/2012 | Karasiuk et al. | |
| 8,221,437 B2 | 7/2012 | Waldron et al. | |
| 8,236,008 B2 | 8/2012 | Boone, III et al. | |
| 8,277,287 B2 | 10/2012 | Hart | |
| 8,337,513 B2 | 12/2012 | Shadduck | |
| 8,343,116 B2* | 1/2013 | Ignon et al. | 604/289 |
| 8,814,836 B2* | 8/2014 | Ignon et al. | 604/289 |
| 9,056,193 B2 | 6/2015 | Ignon et al. | |
| 2001/0023351 A1 | 9/2001 | Eilers | |
| 2001/0049511 A1 | 12/2001 | Coleman et al. | |
| 2002/0016601 A1 | 2/2002 | Shadduck | |
| 2002/0041891 A1 | 4/2002 | Cheski | |
| 2002/0058952 A1* | 5/2002 | Weber et al. | 606/131 |
| 2002/0107527 A1 | 8/2002 | Burres | |
| 2002/0133110 A1 | 9/2002 | Citow | |
| 2002/0133176 A1* | 9/2002 | Parkin et al. | 606/131 |
| 2002/0151826 A1 | 10/2002 | Ramey et al. | |
| 2002/0151908 A1 | 10/2002 | Mallett, Sr. | |
| 2002/0188261 A1* | 12/2002 | Hruska | 604/289 |
| 2003/0012415 A1 | 1/2003 | Cossel | |
| 2003/0018252 A1 | 1/2003 | Duchon et al. | |
| 2003/0060834 A1 | 3/2003 | Muldner | |
| 2003/0093040 A1 | 5/2003 | Mikszta et al. | |
| 2003/0093089 A1 | 5/2003 | Greenberg | |
| 2003/0097139 A1 | 5/2003 | Karasiuk | |
| 2003/0167032 A1 | 9/2003 | Ignon | |
| 2003/0187462 A1 | 10/2003 | Chang | |
| 2003/0208159 A1* | 11/2003 | Ignon et al. | 604/140 |
| 2003/0212127 A1 | 11/2003 | Glassman et al. | |
| 2003/0212415 A1 | 11/2003 | Karasiuk | |
| 2004/0010222 A1 | 1/2004 | Nunomura et al. | |
| 2004/0010269 A1 | 1/2004 | Grimes et al. | |
| 2004/0087972 A1 | 5/2004 | Mulholland et al. | |
| 2004/0092895 A1 | 5/2004 | Harmon | |
| 2004/0092959 A1 | 5/2004 | Bernaz | |
| 2004/0097967 A1 | 5/2004 | Ignon | |
| 2004/0122447 A1 | 6/2004 | Harmon et al. | |
| 2004/0143274 A1 | 7/2004 | Shadduck | |
| 2004/0162565 A1 | 8/2004 | Carson et al. | |
| 2004/0166172 A1 | 8/2004 | Rosati et al. | |
| 2004/0219179 A1 | 11/2004 | McDaniel | |
| 2004/0236291 A1 | 11/2004 | Zelickson et al. | |
| 2004/0243149 A1* | 12/2004 | Lee, Jr. | 606/131 |
| 2004/0254587 A1 | 12/2004 | Park | |
| 2004/0267285 A1* | 12/2004 | Chang | 606/131 |
| 2005/0037034 A1 | 2/2005 | Rhoades | |
| 2005/0038448 A1 | 2/2005 | Chung | |
| 2005/0059940 A1 | 3/2005 | Weber et al. | |
| 2005/0084509 A1 | 4/2005 | Bernstein | |
| 2005/0148958 A1 | 7/2005 | Rucinski | |
| 2005/0203111 A1 | 9/2005 | David | |
| 2005/0209611 A1 | 9/2005 | Greenberg | |
| 2005/0283176 A1 | 12/2005 | Law | |
| 2006/0002960 A1 | 1/2006 | Zoeteweij et al. | |
| 2006/0116674 A1 | 6/2006 | Goble et al. | |
| 2006/0161178 A1* | 7/2006 | Lee | 606/131 |
| 2006/0189964 A1 | 8/2006 | Anderson et al. | |
| 2006/0191562 A1 | 8/2006 | Nunomura | |
| 2006/0200099 A1 | 9/2006 | La Bianco et al. | |
| 2006/0200172 A1 | 9/2006 | Shadduck | |
| 2006/0200173 A1 | 9/2006 | Shadduck | |
| 2006/0212029 A1 | 9/2006 | Arcusa Villacampa et al. | |
| 2006/0253125 A1 | 11/2006 | Ignon | |
| 2006/0264893 A1 | 11/2006 | Sage, Jr. et al. | |
| 2007/0005078 A1 | 1/2007 | Hart et al. | |
| 2007/0043382 A1 | 2/2007 | Cheney | |
| 2007/0065515 A1 | 3/2007 | Key | |
| 2007/0088371 A1* | 4/2007 | Karasiuk | 606/131 |
| 2007/0123808 A1 | 5/2007 | Rhoades | |
| 2007/0154502 A1 | 7/2007 | Hattendorf et al. | |
| 2007/0156124 A1* | 7/2007 | Ignon et al. | 606/9 |
| 2007/0178121 A1 | 8/2007 | First et al. | |
| 2007/0198031 A1 | 8/2007 | Kellogg | |
| 2007/0208353 A1 | 9/2007 | Shadduck | |
| 2007/0239513 A1 | 10/2007 | Khalaj | |
| 2008/0027328 A1* | 1/2008 | Klopotek et al. | 600/472 |
| 2008/0091179 A1 | 4/2008 | Durkin et al. | |
| 2008/0103563 A1 | 5/2008 | Powell | |
| 2008/0119781 A1 | 5/2008 | King | |
| 2008/0132914 A1 | 6/2008 | Bossard et al. | |
| 2008/0139974 A1 | 6/2008 | Da Silva | |
| 2008/0154161 A1 | 6/2008 | Abbott | |
| 2008/0193493 A1 | 8/2008 | Rhoades | |
| 2008/0200861 A1 | 8/2008 | Shalev et al. | |
| 2008/0208146 A1 | 8/2008 | Brandwein et al. | |
| 2008/0214987 A1 | 9/2008 | Xu | |
| 2008/0215068 A1 | 9/2008 | Hart et al. | |
| 2008/0221548 A1 | 9/2008 | Danenberg et al. | |
| 2008/0243039 A1 | 10/2008 | Rhoades | |
| 2008/0287864 A1 | 11/2008 | Rosenberg | |
| 2008/0300529 A1 | 12/2008 | Reinstein | |
| 2008/0300552 A1 | 12/2008 | Cichocki et al. | |
| 2009/0048557 A1 | 2/2009 | Yeshurun et al. | |
| 2009/0053390 A1 | 2/2009 | Sakou et al. | |
| 2009/0062815 A1* | 3/2009 | Karasiuk | A45D 34/04 606/131 |
| 2009/0099091 A1 | 4/2009 | Hantash | |

(56) References Cited

U.S. PATENT DOCUMENTS

| | | |
|---|---|---|
| 2009/0099093 A1 | 4/2009 | Hantash |
| 2009/0124985 A1 | 5/2009 | Hasenoehrl et al. |
| 2009/0138026 A1 | 5/2009 | Wu |
| 2009/0177171 A1 | 7/2009 | Ignon et al. |
| 2009/0192442 A1* | 7/2009 | Ignon et al. .................. 604/22 |
| 2009/0222023 A1 | 9/2009 | Boone, III et al. |
| 2010/0045427 A1 | 2/2010 | Boone, III et al. |
| 2010/0049177 A1 | 2/2010 | Boone, III et al. |
| 2010/0049210 A1 | 2/2010 | Boone, III et al. |
| 2010/0217357 A1 | 8/2010 | Da Silva |
| 2011/0054490 A1 | 3/2011 | Hart |
| 2011/0066162 A1 | 3/2011 | Cohen |
| 2011/0082415 A1 | 4/2011 | Ignon et al. |
| 2012/0022435 A1 | 1/2012 | Ignon et al. |
| 2012/0041338 A1 | 2/2012 | Chickering, III et al. |
| 2012/0136374 A1 | 5/2012 | Karasiuk |
| 2013/0018317 A1 | 1/2013 | Bobroff et al. |
| 2013/0066336 A1 | 3/2013 | Boone, III et al. |
| 2013/0096577 A1 | 4/2013 | Shadduck |
| 2013/0102978 A1 | 4/2013 | Ignon et al. |
| 2013/0144280 A1 | 6/2013 | Eckhouse et al. |
| 2013/0158547 A1* | 6/2013 | David .......................... 606/41 |
| 2014/0343481 A1 | 11/2014 | Ignon |
| 2014/0343574 A1 | 11/2014 | Ignon et al. |
| 2015/0032047 A1 | 1/2015 | Ignon et al. |
| 2015/0230824 A1 | 8/2015 | Shadduck |
| 2015/0230825 A1 | 8/2015 | Shadduck |
| 2015/0231379 A1 | 8/2015 | Ignon et al. |
| 2015/0265822 A1 | 9/2015 | Ignon et al. |
| 2015/0272623 A1 | 10/2015 | Ignon et al. |
| 2015/0290442 A1 | 10/2015 | Ignon et al. |
| 2016/0038183 A1 | 2/2016 | Ignon et al. |

FOREIGN PATENT DOCUMENTS

| | | |
|---|---|---|
| DE | 10 2004 01581 A1 | 11/2005 |
| EP | 0 258 901 | 9/1987 |
| EP | 0 564 392 | 3/1993 |
| IT | 553 076 | 12/1956 |
| IT | 118 49 22 | 3/1985 |
| JP | 1993-088552 | 12/1993 |
| JP | 1997-294747 | 11/1997 |
| JP | 2003-339713 | 12/2003 |
| JP | 2006-503627 | 2/2006 |
| JP | 2006-204767 | 10/2006 |
| KR | 20-0280320 | 7/2002 |
| WO | WO 00/15300 | 3/2000 |
| WO | WO 01/93931 | 12/2001 |
| WO | WO 03/073917 | 9/2003 |
| WO | WO 2004/037098 | 5/2004 |
| WO | WO 2005/070313 | 8/2005 |
| WO | WO 2006/018731 | 2/2006 |
| WO | WO 2007/114904 | 10/2007 |
| WO | WO 2012/145667 | 10/2012 |

OTHER PUBLICATIONS

Cox III et al., *Decreased Splatter in Dermabrasion*, Arch Facial Plastic Surgery, Jan.-Mar. 2000, vol. 2, pp. 23-26.

Ditre et al., *Effect of α-hydroxy acids on photoaged skin: A pilot clinical, histologic, and ultrastructural study*, Journal of American Academy of Dermatology, Feb. 1996, vol. 34, No. 2, Part 1, pp. 187-195.

Harris et al., *Combining Manual Dermasanding with Low Stregnth Trichloroacetic Acid to Improve Antinically Injured Skin*, The Journal of Dermatologic Surgery and Oncology, Jul. 1994, vol. 20, No. 7, pp. 436-442.

\* cited by examiner

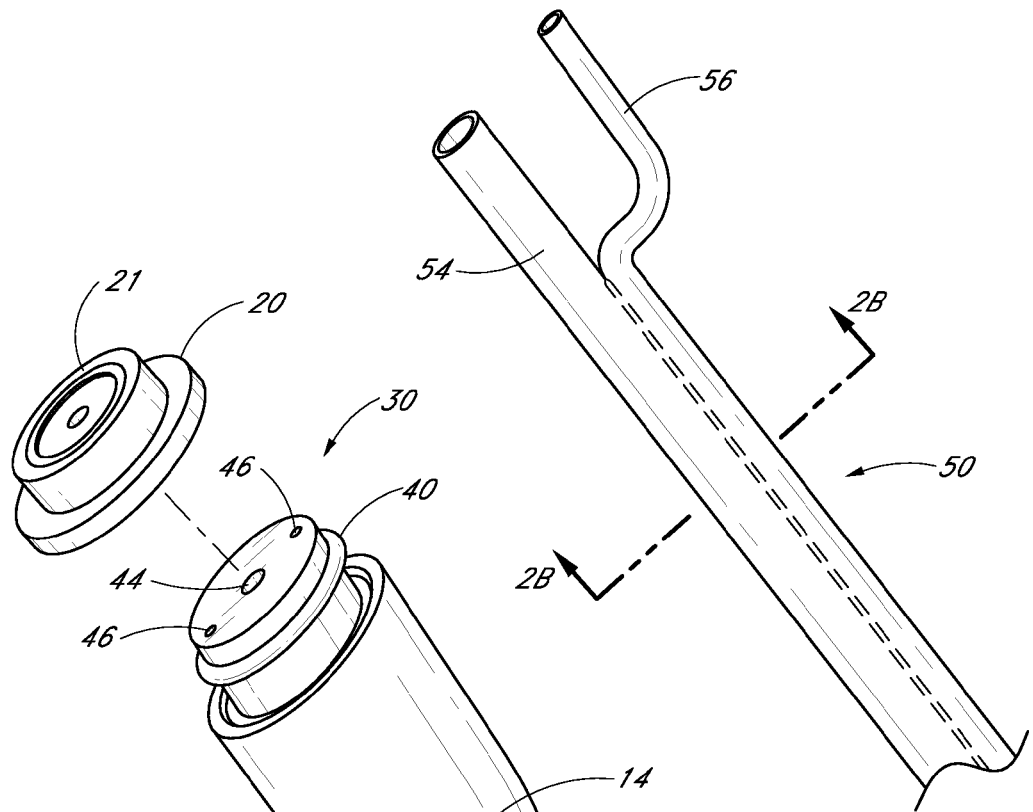
FIG. 2A
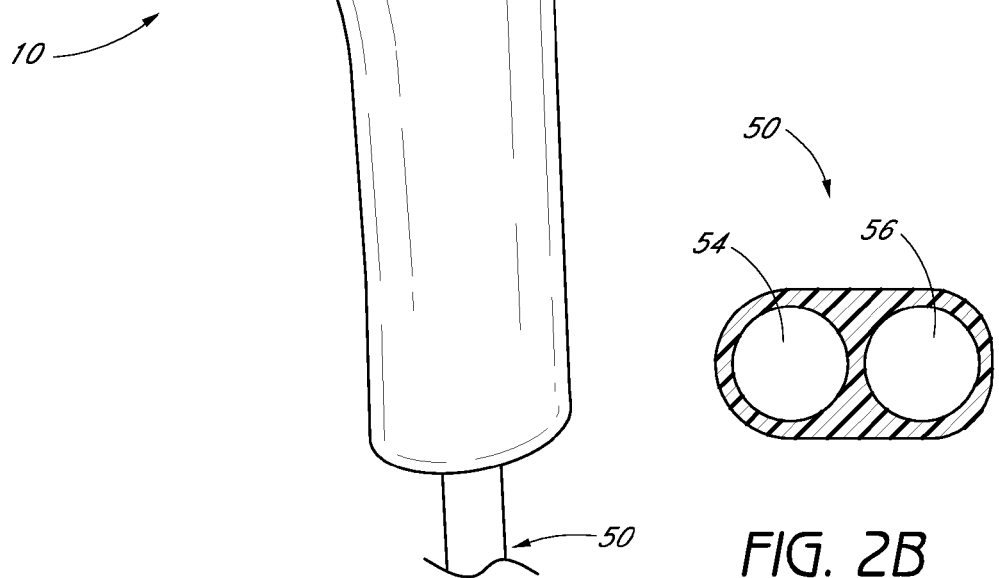
FIG. 1
FIG. 2B

MICRODERMABRASION APPARATUS AND METHOD

CROSS-REFERENCE TO RELATED APPLICATIONS

This application is continuation of U.S. patent application Ser. No. 12/346,582, filed Dec. 30, 2008, which claims the priority benefit under 35 U.S.C. §119(e) of U.S. Provisional Application No. 61/019,196, filed Jan. 4, 2008 and U.S. Provisional Application No. 61/022,201, filed Jan. 18, 2008, the entireties of which are hereby incorporated by reference herein.

BACKGROUND

1. Field of the Inventions

This application relates in general to the field of skin treatment, and more specifically to apparatuses and methods for treating a person's skin.

2. Description of the Related Art

Abrasion of the outer layer or epidermis of the skin is desirable to smooth or blend scars, blemishes, or other skin conditions that may be caused by, for example, acne, sun exposure, and aging. Standard techniques used to abrade the skin have generally been separated into two fields referred to as dermabrasion and microdermabrasion. Both techniques remove portions of the epidermis called the stratum corneum, which the body interprets as a mild injury. The body then replaces the lost skin cells, resulting in a new outer layer of skin. Additionally, despite the mild edema and erythema associated with the procedures, the skin looks and feels smoother because of the new outer layer of skin.

Dermabrasion refers to a procedure in which the surface of the skin is removed due to mechanical rubbing by a handpiece with an abrasive element that is often in the form of a burr, wheel, or disc. This process tends to be painful and messy. In fact, the procedure is sometimes painful enough to require a local anesthetic. Dermabrasion leaves the skin red and raw-looking. The removed skin can take several months to regrow and heal. Recent efforts have led to the use of lasers instead of abrasive elements, which have resulted in less bleeding, but the pain and mess remains.

Efforts have been made to decrease the mess caused by the process waste, such as removed skin and blood, by adding a suction element. As the process waste is drawn into the suction opening, skin that has not been removed is also pulled against the grit surrounding the suction opening, so the procedure remains fairly messy due to the abrasion that takes place outside of the handpiece by the grit.

Microdermabrasion refers generally to a procedure in which the surface of the skin is removed due to mechanical rubbing by a handpiece emitting a stream of sand or grit. For example, a handpiece can be used to direct an air flow containing tiny crystals of aluminum oxide, sodium chloride, or sodium bicarbonate. The momentum of the grit tends to wear away two to three cell layers of the skin with each pass of the handpiece. Alternatively, new "crystal-free" microdermabrasion techniques utilize a diamond-tipped handpiece without a stream of grit.

Efforts to add a suction element have been more successful in microdermabrasion than in dermabrasion because the handpiece applying the stream of grit is more controllable to a localized area. That is, as the removed skin is drawn into the suction opening, skin that has not been removed is also pulled towards the handpiece where it is treated with the grit stream, allowing for simultaneous local treatment and suction.

Microdermabrasion removes moisture from the skin, so the procedure is always followed by the application of moisturizing creams. However, similar to topical application of moisturizing creams prior to microdermabrasion, the moisturizing elements only work as deep as the active ingredients can passively migrate through the remaining epidermis.

SUMMARY

According to some embodiments, a system for treating skin includes a handpiece assembly comprising a tip and a main body portion, the main body portion comprising an interior cavity and a canister configured to store at least one treatment or waste material. The treatment or waste material is in fluid communication with the tip.

In some embodiments, the system further comprises a fluid transfer device for transferring the treatment or waste material to and from the canister. In other embodiments, the system further includes a conduit configured to place the canister in fluid communication with the tip. In still other arrangements, the conduit is routed within the interior cavity of the main body portion. In another embodiment, the conduit comprises at least two passages with each passage configured to transfer a different material to or from the canister.

According to some embodiments, the handpiece assembly and the canister form a unitary structure. In alternative embodiments, the handpiece assembly and the canister are substantially separated. In one embodiment, the canister comprises at least one compartment which may be configured to contain a treatment fluid and/or waste materials. In other embodiments, the treatment fluid comprises a serum. In yet other arrangements, the tip of the handpiece assembly is removable.

BRIEF DESCRIPTION OF THE DRAWINGS

These and other features, aspects and advantages of the present invention are described with reference to drawings of certain preferred embodiments, which are intended to illustrate, but not to limit, the present invention. The drawings include twenty-eight (28) figures. It is to be understood that the attached drawings are for the purpose of illustrating concepts of the present invention and may not be to scale.

FIG. 1 illustrates a perspective view of a handpiece assembly for use in a skin treatment system according to one embodiment;

FIG. 2A illustrates a perspective view of one embodiment of a conduit adapted for use in the handpiece assembly of FIG. 1;

FIG. 2B illustrates a cross-sectional view of one embodiment of the tubing of FIG. 2A;

DETAILED DESCRIPTION OF THE PREFERRED EMBODIMENTS

Figure 3:
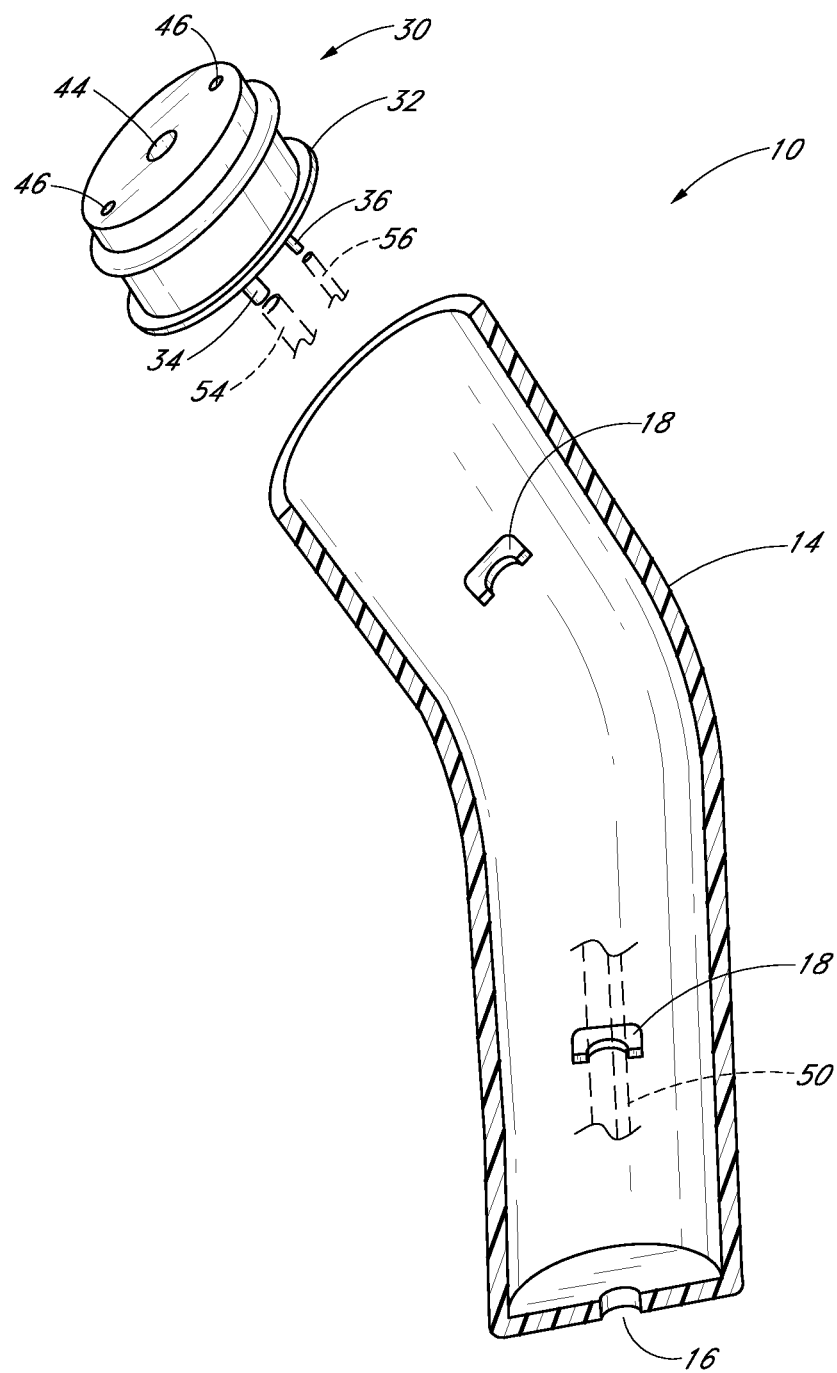
FIG. 3 illustrates a perspective view of a handpiece assembly with a portion of the exterior surface removed to reveal an interior portion of the assembly according to one embodiment.

FIG. 1 illustrates one embodiment of a handpiece assembly 10 configured for use in a skin treatment system which may be used to perform one or more treatments on a person's skin. In the depicted embodiment, the handpiece assembly 10 comprises an outer housing 14 that can be grasped or otherwise manipulated by a user. As shown, the housing 14 can include a curved shape. In other embodiments, the shape, size and/or other details regarding the housing 14 can vary as desired.

With continued reference to FIG. 1, the handpiece assembly 10 can include a tip 20 that is configured to contact or substantially contact the skin or other surface being treated. According to some embodiments, as illustrated in FIG. 1, the tip 20 can be removable. Thus, the tip 20 can be easily changed for cleaning, hygienic or other purposes. For example, depending on the type of skin treatment procedure being performed, a user can select a tip 20 having a specific pattern or features along the distal end. Non-limiting examples of the various types of tips 20 that may be attached to the handpiece assembly 10 are disclosed in U.S. patent application Ser. No. 11/392,348, filed Mar. 29, 2006, the entirety to which is hereby incorporated by reference herein.

In arrangements where a removable tip 20 is used, the handpiece assembly 10 can include an interface portion 30 along its distal end that is configured to securely receive the tip 20. In FIG. 1, the interface portion 30 comprises an O-ring 40 or other sealing member to help prevent or reduce the likelihood of leaks. In other embodiments, one or more other types of gaskets or similar devices can be used, either in lieu of or in addition to an O-ring 40.

With continued reference to FIG. 1, the interface portion 30 can include one or more openings 44, 46 or ports. In some embodiments, these openings 44, 46 are configured to transfer fluids and/or other materials to and/or from the tip 20. For example, in the depicted embodiment, the interface portion 30 comprises two fluid delivery openings 44 positioned along the periphery and one fluid suction opening 46 positioned along the center of the handpiece assembly 10. In other embodiments, however, the number, location, spacing, shape, size and/or other details of the openings 44, 46 can vary as desired or required.

One or more conduits 50 can be placed in fluid communication with the openings 44, 46, and thus, at least a portion of the tip 20 of the handpiece assembly 10. The conduits 50 can be configured to transfer (e.g., deliver, withdraw, etc.) fluids or other materials to and/or from the distal end of the handpiece assembly 10. As shown in FIG. 1, the conduit 50 can be positioned at least partially within an interior portion of a handpiece assembly 10. In the depicted embodiment, the conduit 50 extends out of the proximal end of the handpiece assembly 10.

FIG. 2A illustrates one embodiment of a conduit 50 that is configured for use in a handpiece assembly 10. As shown, the conduit 50 can include a delivery passage 54 and a suction passage 56. In other embodiments, the conduit 50 can comprise more or fewer passages, as desired or required by a particular application or use. In addition, the size, shape and other details of the passages 54, 56 can be different than illustrated in FIGS. 2A and 2B. The conduit 50 can comprise tubing, pipe and/or the like. Further, the conduit 50 can include one or more rigid, semi-rigid and/or flexible materials, such as, for example, rubber, plastic, other polymeric materials, other synthetic materials, metal or the like.

With continued reference to FIG. 2A, the various passages 54, 56 of the conduit 50 can be co-molded or otherwise produced as a unitary structure. In FIG. 2A, the passages 54, 56 are attached to each other along a portion of the conduit 50 and separated from each other along another portion of the conduit 50. According to some embodiments, the conduit 50 can be manufactured using extrusion or other production method. In other arrangements, individual passages that connect to the handpiece assembly 10 are separate members that may or may not be attached to one another. For example, in one embodiment, the passages 54, 56 can comprise separate rubber tubing portions that are joined to each other using adhesives, clips, tape, fasteners and/or one or more other attachment methods or devices. The shape, size and/or other details of the passages 54, 56 can be different than illustrated herein.

FIG. 3 illustrates an exploded perspective view of the handpiece assembly 10 of FIG. 1 with a portion of the outer housing 14 removed to reveal an interior area. As shown, an interior of the handpiece assembly 10 can comprise one or more tabs 18, guides, other fasteners and/or other members that are shaped, sized and otherwise configured to receive and secure one or more conduits 50 extending within the assembly 10. By way of example, in FIG. 3, a small portion of a conduit 50 is shown (in phantom) within one of the tabs 18. In the illustrated embodiment, the handpiece assembly 10 includes a total of two tabs 18. However, the quantity, type, shape, size and/or other details of the tabs 18 or other members can vary. Further, the proximal end of the handpiece assembly 10 can comprise an opening 16 or other slot through which a conduit 50 and/or other items can extend.

With continued reference to FIG. 3, the interface portion 30 of the handpiece assembly 10 can include one or more ports 34, 36 that are configured to attach to passages 54, 56 of a conduit 50. For example, in FIG. 3, the delivery passage 54 is shown (in phantom) as being associated with a first port 34 and the suction passage 56 is shown (in phantom) as being associated with a second port 36. In other embodiments, a handpiece assembly 10 comprises more or fewer ports, as desired or required. In addition, the size, shape, type and/or other details of the ports can vary. In some embodiments, once the tubing 50 is properly secured to the ports 34, 36 of the handpiece assembly, the delivery passage 54 can be placed in fluid communication with the one or more delivery openings 44. Likewise, the suction passage 56 can be placed in fluid communication with the one or more suction openings 46. Consequently, one or more fluids or other materials can be selectively transferred (e.g., delivered to and/or removed from) the tip 20 of the handpiece assembly 10.

As illustrated in FIG. 3, the assembly 10 can be configured such that a single port 36 can be in fluid communication with two or more openings 46 located along a distal surface of the interface portion 30. In other embodiments, a single opening along the distal surface of the interface portion 30 can be in fluid communication with two or more ports. Thus, the interface portion 30 can include one or more internal channels, flow splitting devices, flow control valves and/or any other devices or features that can selectively affect the flow of fluids therethrough. This can apply to delivery and/or suction ports and openings, as desired or required by a particular application.

The use of a conduit 50 that extends within an interior cavity of the handpiece assembly 10 can provide one or more advantages or benefits. For example, such designs can permit a user to easily remove, attach or replace a conduit 50 between or during a treatment or procedure. In addition, contamination of an interior of the handpiece assembly 10 can be reduced or eliminated because fluids or other substances transmitted through the handpiece assembly 10 are fully contained within the passages 54, 56 of the conduit 50.

Figure 4:
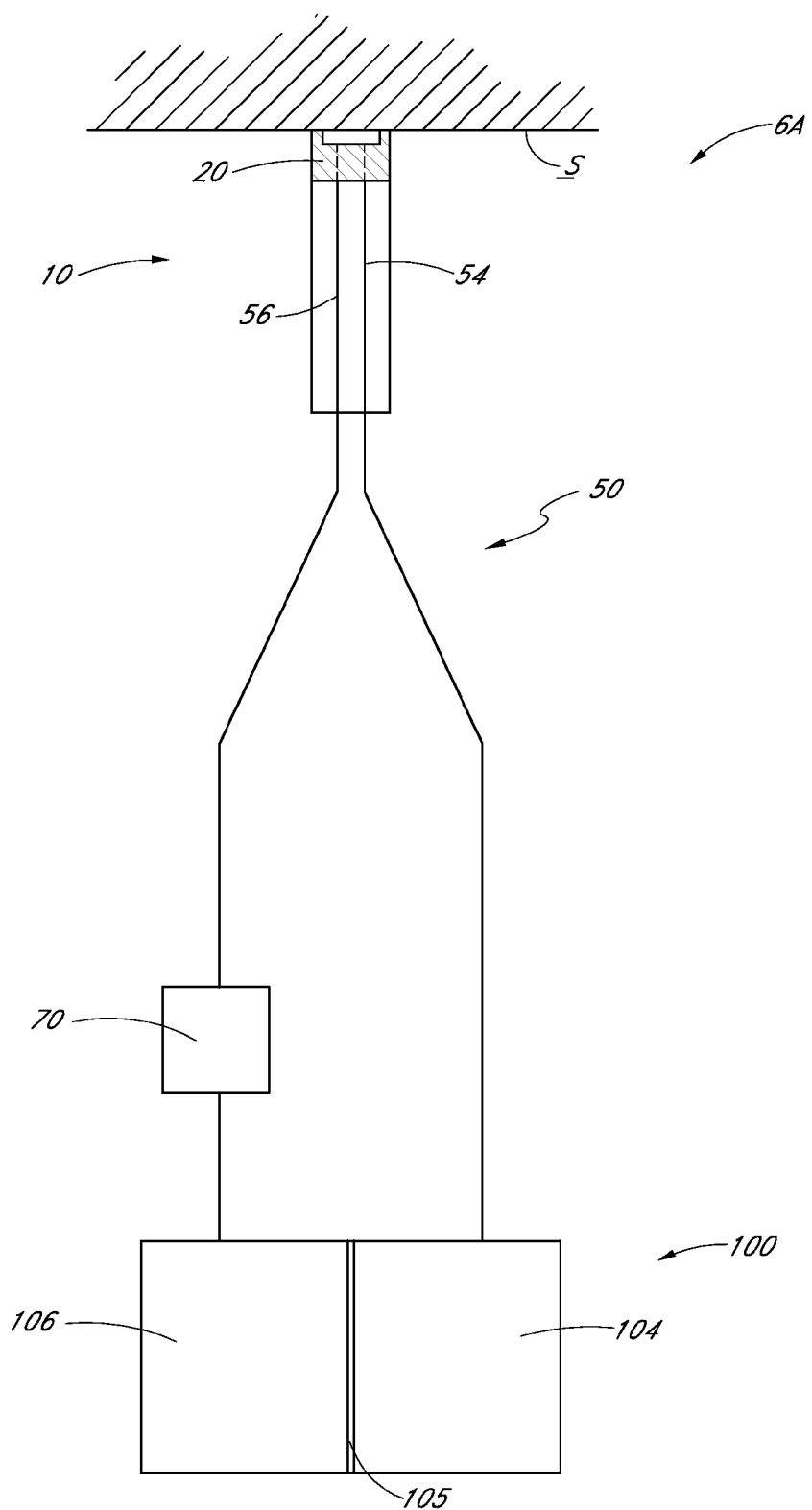
FIG. 4 schematically illustrates one embodiment of a skin treatment system according to one embodiment.

FIG. 4 schematically illustrates one embodiment of a skin treatment system 6A. The depicted treatment system 6A comprises a handpiece assembly 10, a conduit 50, a fluid transfer device 70 (e.g., pump) in fluid communication with the conduit 50 and a canister 100 or other container. As shown, the handpiece assembly 10 can include a tip 20 that is adapted to contact and treat the skin S. A conduit 50 having a delivery passage 54 and a suction (e.g., removal) passage 56 can be attached to the handpiece assembly 10 and placed in fluid communication with the tip 20. In addition, a pump 70 or other fluid transfer device can be placed in fluid communication with the conduit 50 (e.g., the suction passage 56) to assist in transferring fluids or other materials to and/or from the tip 20.

With continued reference to FIG. 4, the canister 100 or other container can comprise a storage compartment 104 and a waste compartment 106. In other arrangements, the canister 100 can include more or fewer compartments, as desired or required. For example, the canister 100 can include two or more storage compartments, each of which is configured to store a different fluid and/or other treatment media. In some embodiments, the canister 100 comprises a unitary structure having one or more baffles 105 or other dividing members to create two or more separate compartments 104, 106. However, in other embodiments, the system 6A comprises two or more separate canisters that are not part of a unitary structure or that are not attached to each other.

In FIG. 4, when the tip 20 is placed against the surface of the skin S to be treated, a pump 70 or other fluid transfer device can be used to draw a treatment media (e.g., water, saline, other fluids, other materials, etc.) from the storage compartment 104 and through the delivery passage 54. At the same time, the pump 70 can remove waste materials from the treatment surface to the waste compartment 106 via the suction passage 56. In other embodiments, one or more other methods and/or devices for delivering and/or withdrawing fluid or other materials to and/or from the distal end of the handpiece assembly 10 can be used.

Figure 5:
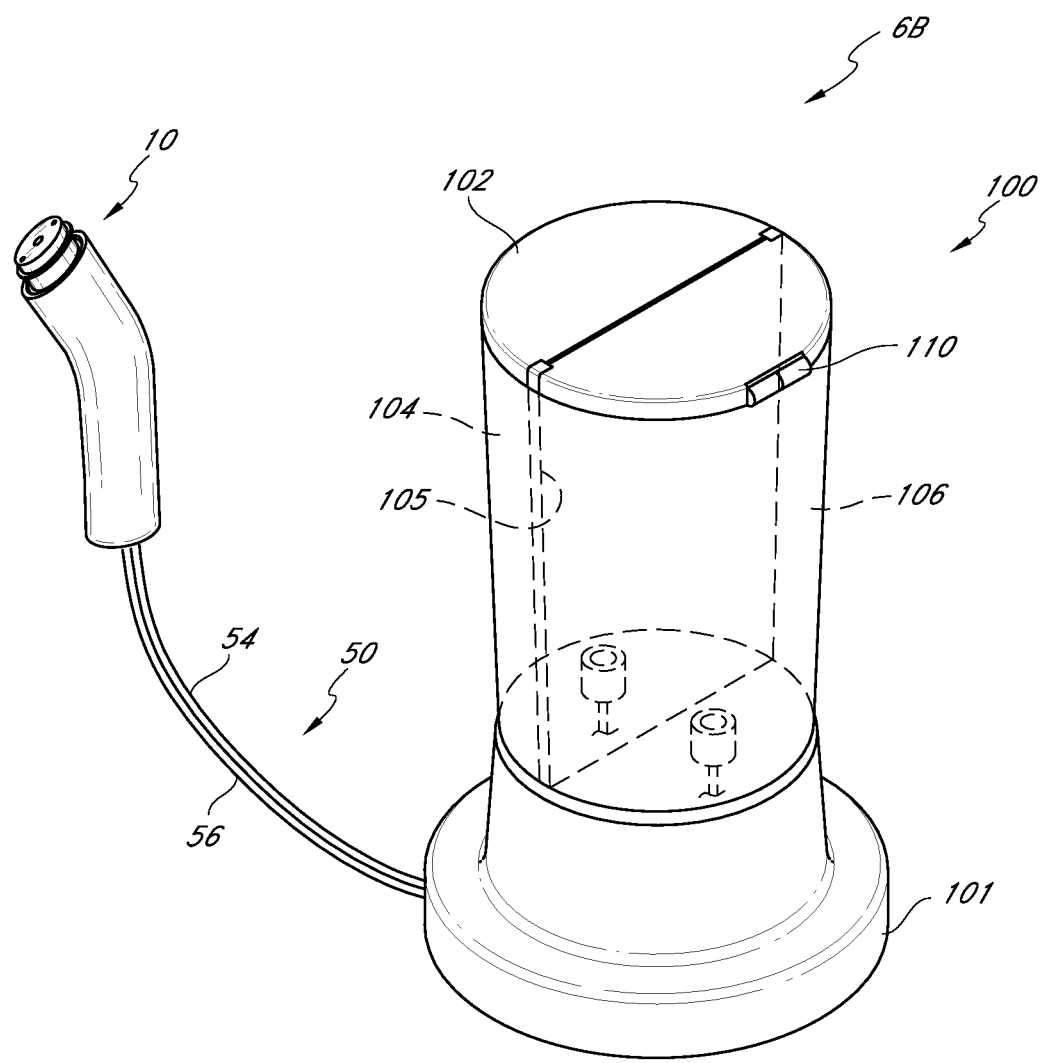
FIG. 5 illustrates a perspective view of a skin treatment system comprising a handpiece assembly and a canister according to one embodiment.

As illustrated in FIG. 5, a handpiece assembly 10 and a conduit 50 of a treatment system 6B can be placed in fluid communication with a canister 100. The illustrated canister 100 comprises a base 101 and one or more compartments 104, 106. As discussed, the canister 100 can include one or more storage compartments 104 and/or waste compartments 106 that are separated by a baffle 105 or other separation member. The various compartments 104, 106 can be placed in fluid communication with one or more passages 54, 56 of the conduit 50 to selectively transfer fluids and/or other materials to and/or from a handpiece assembly 10. In addition, the system 6B can include a pump or other fluid transfer device (not shown). For example, in one embodiment, a pump is placed within or near the base 101. In other arrangements, the pump is positioned in one or more other locations (e.g., external to the base 101).

With continued reference to FIG. 5, the canister 100 can include a lid 102 or other cover member that permits a user to selectively access the interior of the compartments 104, 106 for filling, emptying, cleaning and/or any other task. In some embodiments, the lid 102 comprises a hinge 110 or other device that facilitates accessing the interior of the various compartments 104, 106.

Figure 6A:
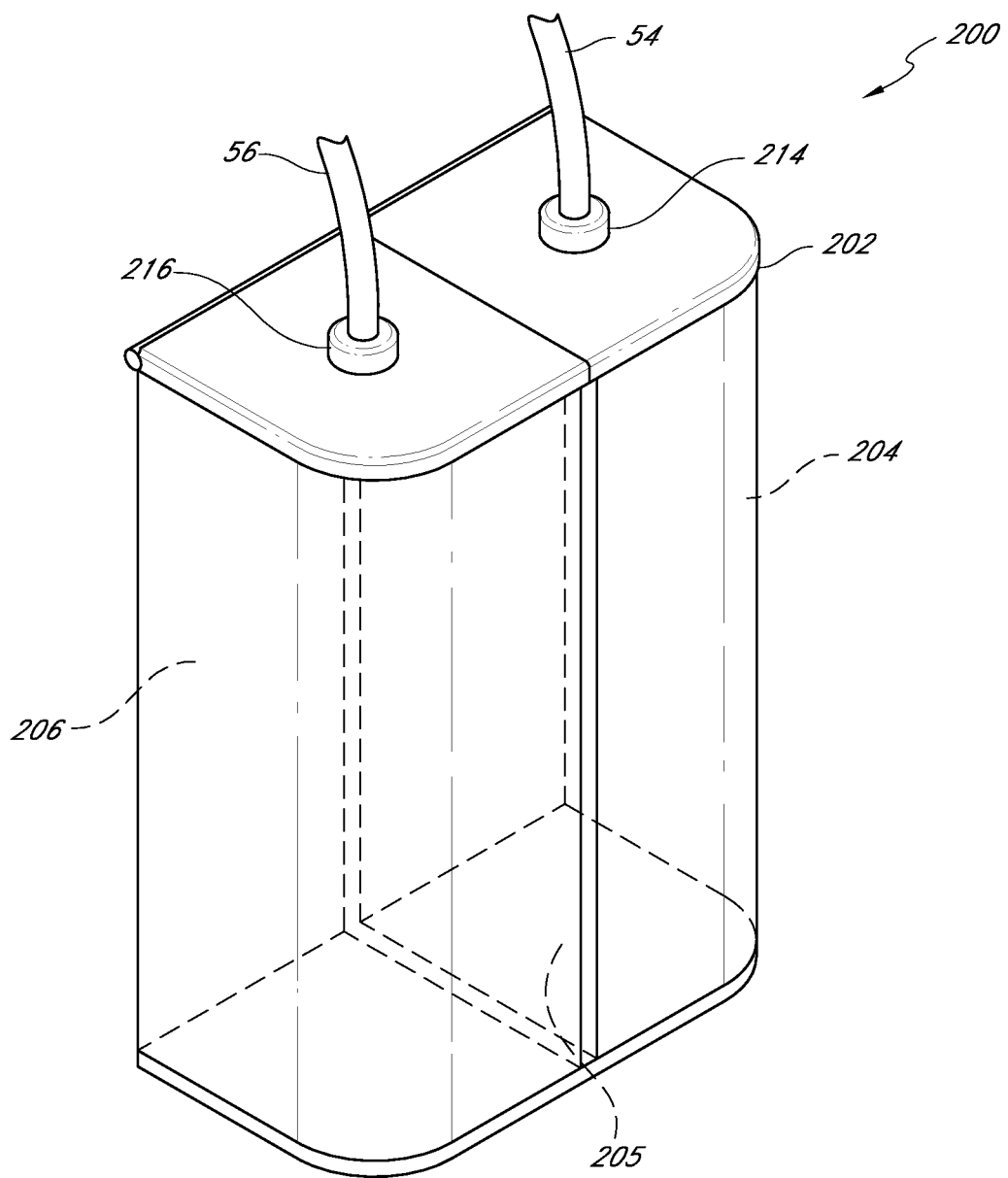
FIG. 6A illustrates a perspective view of a combination storage and waste canister in accordance with another embodiment.

Another embodiment of a canister 200 is illustrated in FIG. 6A. In the depicted arrangement, the canister 200 comprises a storage compartment 204 and a waste compartment 206. As discussed, however, in other embodiments, the canister 200 can comprise more or fewer compartments, as desired or required. The compartments 204, 206 can be separated by a baffle 205 or another separation member. In addition, the canister can include a removable lid 202 that permits a user to access the interior of the compartments 204, 206. In FIG. 6A, each compartment 204, 206 comprises a fitting 214, 216 or similar member to which conduits or passages 54, 56 of a conduit (e.g., tubing, pipe, etc.) can attach. Thus, the conduit can be placed in fluid communication with the various compartments 204, 206 of the canister 200. In other embodiments, the fittings 214, 216 or ports can be located in one or more other locations of the canister 200 (e.g., the bottom, side, etc.).

Figure 6B:
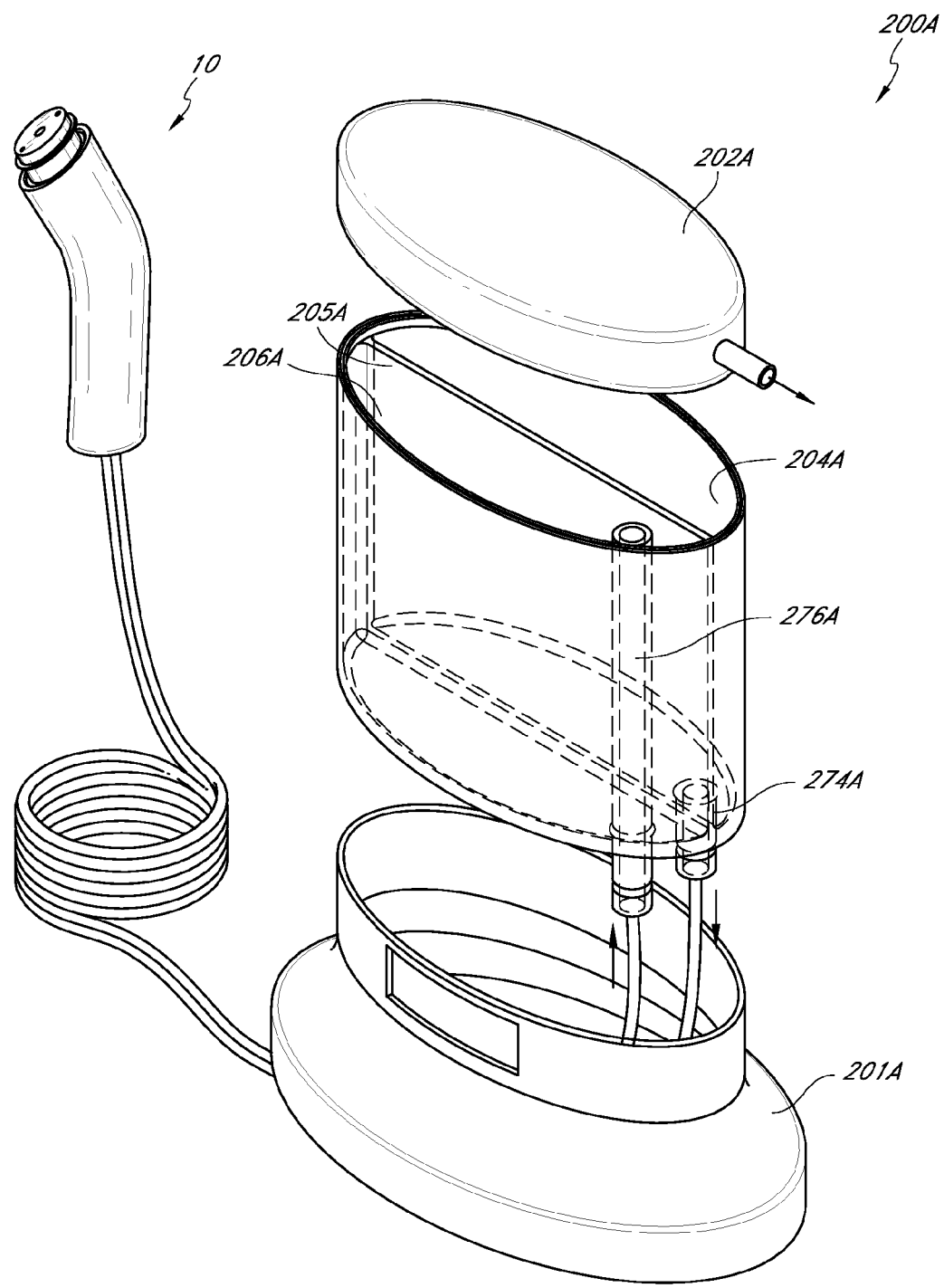
FIG. 6B illustrates a perspective view of a combination storage and waste canister in accordance with yet another embodiment.

A different embodiment of a canister 200A is illustrated in FIG. 6B. As with other embodiments, the illustrated canister 200A comprises a supply compartment 204A and a waste compartment 206A that are separated by a baffle 205A or other member. As shown, the canister 200A can comprise a base 201A and a lid 202A or other cover member. In addition, the compartments 204A, 206A can comprise one or more internal channels or conduits 274A, 276A that facilitate in the transfer of fluids or other materials into and/or out of the canister 200A. In some embodiments, the canister 200A is configured to move fluids to and from a handpiece assembly 10 in a manner similar to what is schematically described in FIG. 4.

Figure 7:
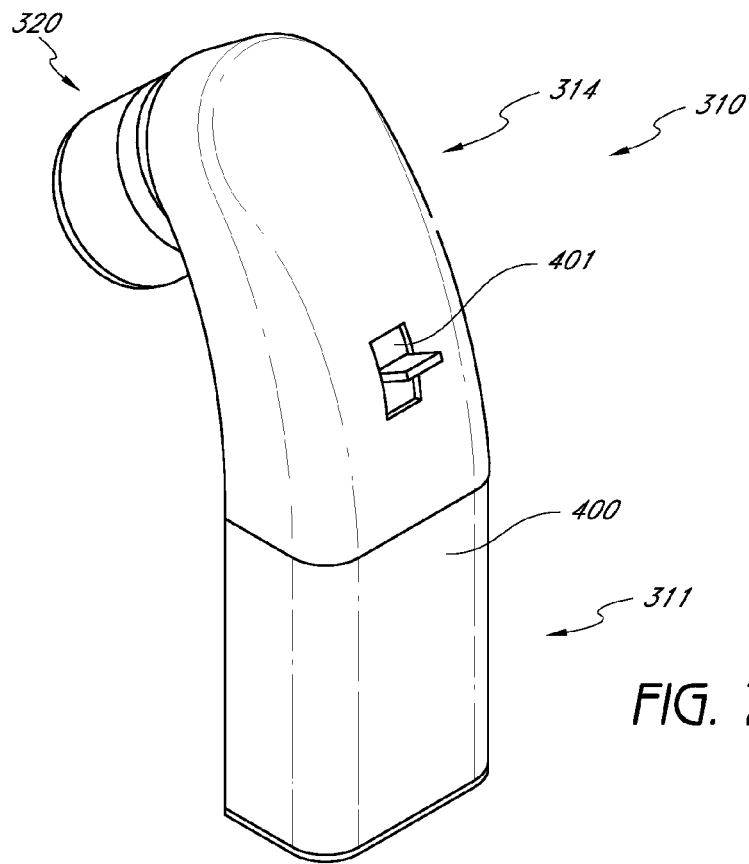
FIG. 7 illustrates a perspective view of another embodiment of a handpiece assembly.

FIG. 7 illustrates a handpiece assembly 310 according to another embodiment. In the depicted arrangement, the handpiece assembly 310 comprises a main body portion 314 and a tip 320 that is configured to contact and treat the skin. In addition, in the illustrated embodiment, the proximal end 311 of the assembly 310 includes a canister 400. Thus, unlike other arrangements disclosed herein, the depicted canister 400 is physically attached to and incorporated into the handpiece assembly 310. In one embodiment, the canister 400 can be separated and/or attached to the main body portion 314 of the handpiece assembly 310 by manipulating a release tab 401, button or other feature. One or more gaskets, O-rings or other members (not shown) can be positioned between the main body portion 314 and the canister 400 in order to reduce the likelihood of leaks.

Accordingly, a user can easily and conveniently handle and manipulate the handpiece assembly 310 illustrated in FIG. 7 (or variations thereof) because the canister 400 and the main body portion 314 of the assembly 310 are self contained within a single structure. In some embodiments, the handpiece assembly 310 includes an internal pump or other fluid transfer device within its main body portion 314. Alternatively, a fluid transfer device and/or any other component can be positioned outside of the handpiece assembly 310 and/or at any other location. Such components can be attached to or separate from the handpiece assembly, as desired or required.

Figure 8:
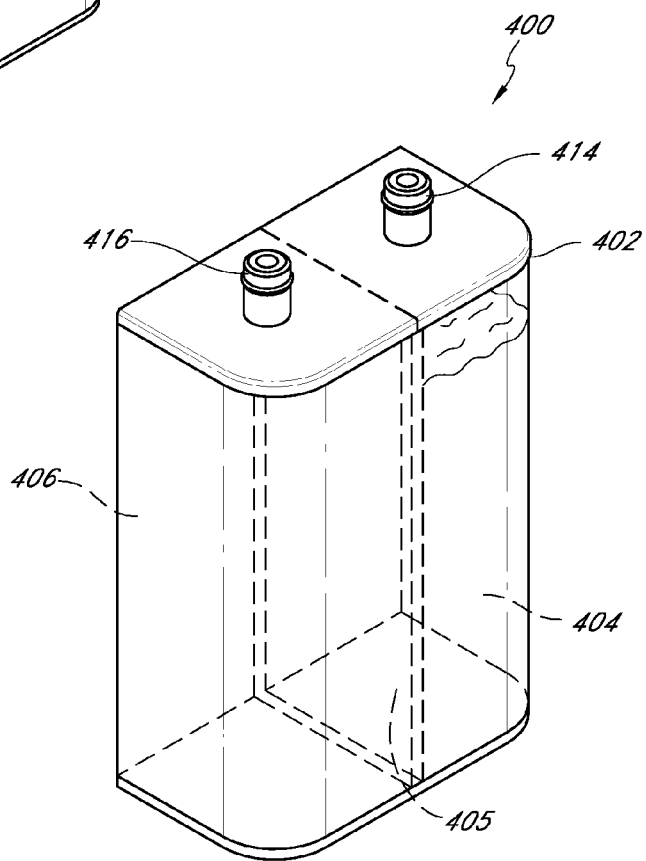
FIG. 8 illustrates a perspective view of an embodiment of a combination storage and waste canister configured to be used with the handpiece assembly of FIG. 7.

FIG. 8 illustrates one embodiment of a canister 400 configured for use with a self-contained handpiece assembly 310 such as the one as illustrated in FIG. 7. As shown, the canister 400 can comprise a delivery compartment 404 in which one or more treatment fluids or other materials can be placed. In addition, the canister 400 can comprise a waste compartment 406 to which fluids, exfoliated skin and/or other substances withdrawn from the treatment surface can be directed. As with other embodiments disclosed herein, the canister 400 can comprise a baffle 405 or other separation member. In other embodiments, completely separate canisters can be attached to the proximal end of the handpiece assembly 310 (e.g., one or more delivery canisters, a waste canister, etc.).

With continued reference to FIG. 8, the canister 400 can comprise one or more ports 414, 416 or other fittings through which fluids or other substances can be transferred (e.g., between the tip 320 and the canister 400). According to some embodiments, the canister 400 is configured to lock to the main body portion 314 using one or more devices or methods, such as, for example, locking tabs, clasps, magnetic connectors, other fasteners and/or the like.

Any of the embodiments of a handpiece assembly disclosed herein can comprise a tip that swivels, rotates and/or otherwise moves relative to a main body portion. Such a feature can facilitate moving and manipulating a handpiece assembly along a person's skin surface during a treatment procedure. This can be particularly significant when the treatment surface is highly contoured.

Figure 9:
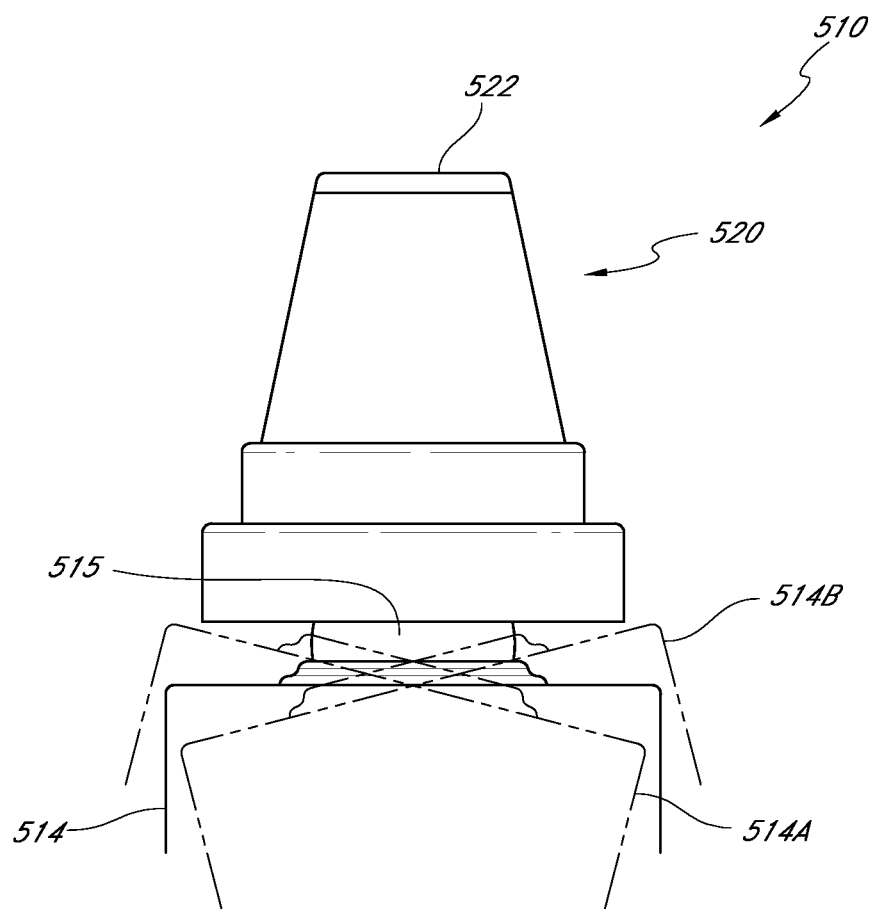
FIG. 9 schematically illustrates one embodiment of the distal end of a handpiece assembly having a tip that is configured to tilt or pivot.

In the embodiment illustrated in FIG. 9, a handpiece assembly 510 comprises a joint 515, hinge or other movement mechanism (e.g., ball joint or mechanism, swivel joint or mechanism, etc.). In the illustrated arrangement, the joint 515 is generally located between the tip 520 and the main body portion 514 of the handpiece assembly 510. As illustrated in phantom, such a joint 515 or other mechanism can advantageously permit a tip 520 to be moved relative to the adjacent body portion 514. For example, in some embodiments, the body portion 514 can be moved relative to the tip 520 between a first position 514A and a second position 514B. In some embodiments, the passages of a conduit (not shown) are configured to pass through the joint 514 (e.g., for passages to be in fluid communication from the main body portion 514 to the tip 520 through the joint 515) to permit fluids or other materials to be transferred to and/or from the working surface 522 of the tip 520 during the operation of the handpiece assembly 510.

With respect to any of the embodiments discussed and/or illustrated herein, the handpiece assembly, pump or other fluid transfer device and/or any other component of the skin treatment system can be powered using one or more power sources. For example, in some embodiments, a battery (e.g., disposable, rechargeable, etc.), an AC power source (e.g., with or without a transformer) or any other power device or source can be connected, attached or otherwise supplied to the desired component or subcomponent of the treatment system. In addition, the various components or subcomponents can include one or more controllers, electrical and/or instrumentation connections, ports and/or the like, as desired or required for the proper operation of the treatment system.

According to one embodiment, the self-contained handpiece assembly 310 illustrated in FIG. 7 is configured to include a rechargeable battery. The handpiece assembly 310 can be sized, shaped and otherwise configured to be placed in a docking station when not in use. The docking station can be configured to recharge the battery of the assembly 310. In other embodiments, however, a handpiece assembly can be powered by AC or DC power (e.g., connected to a power cable or the like).

Figure 10:
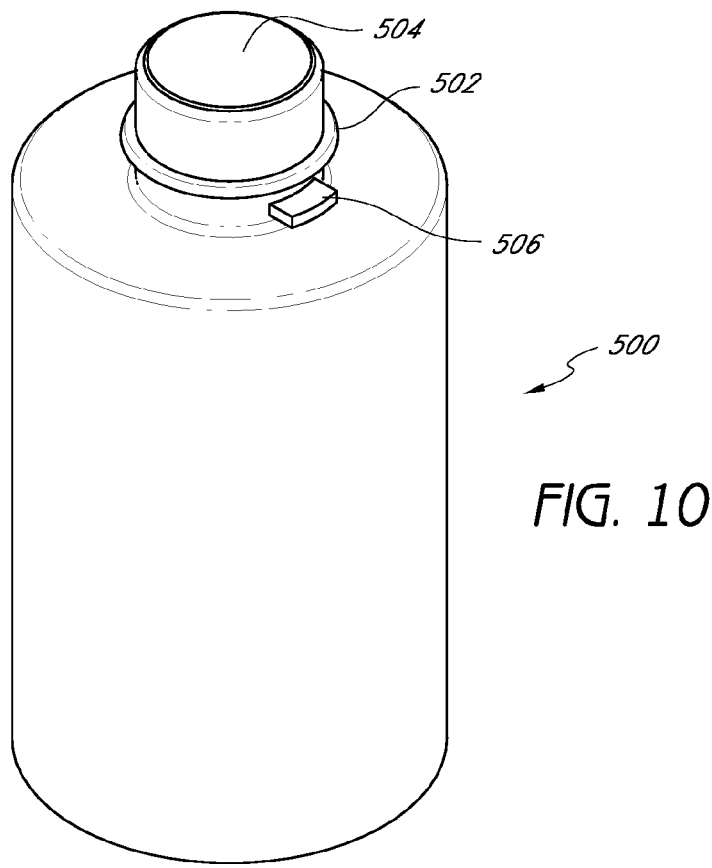
FIG. 10 illustrates a perspective view of a cartridge or other container comprising a treatment fluid or other material according to one embodiment.

FIG. 10 illustrates one embodiment of a cartridge 500 containing a serum and/or another fluid or material used during a skin treatment procedure. As shown, the cartridge 500 can comprise a membrane 504 or other member to seal or substantially seal the internal contents of the cartridge 500. In addition, the cartridge 500 can include a locking ear 506 or other feature or member that is configured to mate with a corresponding portion of the handpiece assembly. In some embodiments, such a locking ear 506 is sized, shaped and otherwise configured to align with a slot or other opening in a docking area of the handpiece assembly. Once the locking ear 506 or other feature is properly aligned with and pushed into a corresponding recess or other portion of the handpiece assembly, the cartridge 500 can be rotated or otherwise moved to secure it to the handpiece assembly. In other arrangements, a cartridge include two or more locking ears 506 or other features that are configured to mate with corresponding areas or portions of the handpiece assembly.

With further reference to FIG. 10, the cartridge 500 can include an O-ring 502 or other sealing member to help prevent fluids and/or other substances from leaking once the cartridge 500 is properly inserted within the handpiece assembly. In the illustrated embodiment, the cartridge 500 comprises a generally cylindrical body with a relatively narrow neck portion. However, it will be appreciated that the shape, size and/or any other details or characteristics of the cartridge 500 can be different than illustrated and discussed herein to suit a particular application or use.

Figure 11:
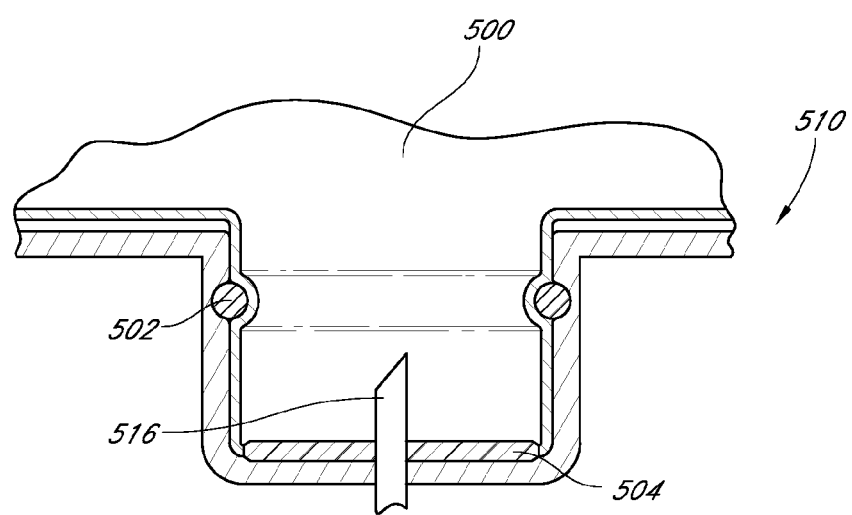
FIG. 11 illustrates a cross-sectional view of a handpiece assembly or other portion of the treatment system configured to receive the cartridge or container of FIG. 10.

FIG. 11 illustrates a cross-sectional view of a docking portion or area 510 of a handpiece assembly with a cartridge 500 being secured therein. As illustrated, the docking area 510 of the handpiece assembly can include a hollow tube 516 or other puncturing member that is configured to penetrate the membrane 504 when the cartridge 500 is securely positioned within the docking area 510. As discussed, in order to prevent or reduce the likelihood of leaks, the nozzle of the cartridge and/or the docking area 510 can comprise an O-ring 502 and/or another sealing member.

According to some embodiments, once the membrane 504 is punctured, the internal contents of the cartridge 500 can be in fluid communication with the tip (not shown) of a handpiece assembly. Thus, the hollow tube 516 or other penetrating member can access the internal contents of the cartridge 500 so they can be transferred through the body of the handpiece assembly to a working surface (e.g., tip). The fluids and/or other substances can be conveyed to a tip or other working surface of the handpiece assembly by gravity flow, using a pump or other fluid transfer device and/or the like. In some arrangements, as illustrated in FIG. 10, the cartridge 500 includes a locking member 506 (e.g., tab) that is configured to mate with a corresponding portion of the docking area 510 when properly inserted therein.

The membrane 504 of the cartridge 500 can include any flexible, semi-rigid or rigid materials that is adapted to be punctured by a hollow tube 516 or other member when the cartridge 500 is secured to a handpiece assembly. In some embodiments, the membrane comprises rubber, plastic and/or the like. In addition, the membrane 504 can be configured to be re-sealable once the cartridge 500 is removed from the handpiece assembly.

Figure 12:
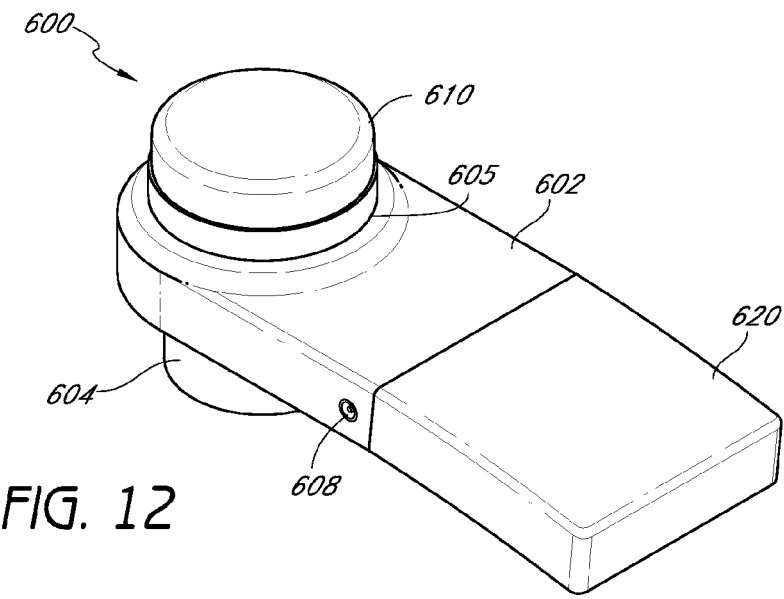
FIG. 12 illustrates a perspective view of a handpiece assembly according to another embodiment.
Figure 13:
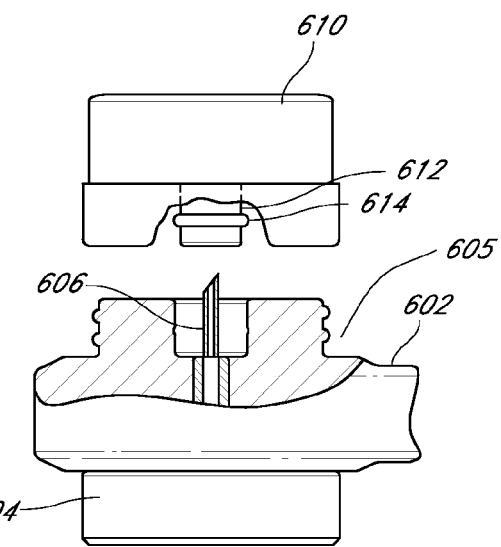
FIG. 13 illustrates a cross-sectional view of a portion of a handpiece assembly configured to receive a cartridge or other container according to one embodiment.
Figure 14:
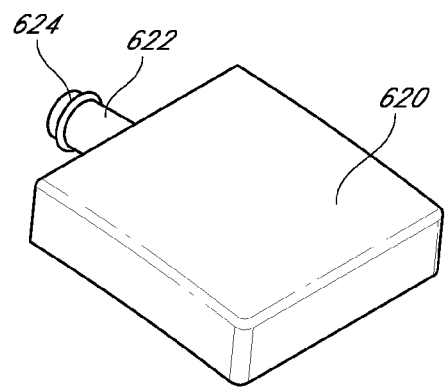
FIG. 14 illustrates a perspective view of waste cartridge or container configured for use with a skin treatment system according to one embodiment.

FIGS. 12-14 illustrate another embodiment of a handpiece assembly 600 adapted to treat the skin. The depicted assembly 600 comprises a main body portion 602, a working tip 604 and a docking area or port 605 in which a cartridge 610 and a waste canister 620 can be inserted. Such a assembly 600, as with other embodiments disclosed herein, can be an all-inclusive assembly that eliminates or reduces the need for other separate components. For example, the main body portion 602 can comprise a vacuum pump or other fluid transfer device (not shown) to help deliver fluids and other treatment materials to the working tip 604 and remove waste fluids, exfoliated skin and/or other materials to the waste canister 620.

With reference to FIG. 13, the handpiece assembly 600 can include a docking port or area 605 that is configured to receive a cartridge 610. The cartridge can include one or more treatment fluids, substances or the like. In some embodiments, as discussed herein with respect to the embodiment illustrated in FIG. 10, the cartridge 610 comprises a membrane (not shown in FIG. 13) that is configured to substantially seal the internal contents of the cartridge 610. The docking area 605 can include a puncturing member 606 (e.g., hollow tube, syringe, needle, etc.) that is sized, shaped, positioned and otherwise configured to break the membrane or seal so that the contents of the cartridge 610 can be placed in fluid communication with the main body portion 602 and the tip 604 of the handpiece assembly 600.

The cartridge 610 and docking area 605 can include one or more mating features (e.g., threads, locking tabs, snap connections, other mechanical fasteners, etc.) to ensure that the cartridge 610 is secured to the handpiece assembly 600 during use.

As illustrated in the cutaway cross-sectional view of FIG. 13, the docking area 605 can be shaped, sized and otherwise configured to receive a nozzle 612 or other protruding member of the cartridge 610. Accordingly, the hollow tube 606 or other puncturing member of the main body portion 602 can penetrate a membrane or other sealing member disposed along the end of the nozzle 612 once the cartridge 610 is secured within the docking area 605. In order to prevent or reduce the likelihood of leaks of fluids and/or other substances contained within the cartridge 610, the nozzle 612 can comprise one or more O-rings 614 or other sealing members.

The handpiece assembly 600 illustrated in FIGS. 12-14 includes a generally rectangular shape. However, in other embodiments, the shape, size and/or other characteristics or properties of the handpiece assembly 600 can vary, as desired or required by a particular application or use.

FIG. 14 illustrates one embodiment of a waste canister 620 that is configured to attach to a proximal end of the handpiece assembly 600. The waste canister 620 can be configured to collect exfoliated skin, used serums and other fluids and/or the like that are drawn away from a person's skin during treatment. As shown, the waste canister 620 can comprise a port 622 that is adapted to engage and secure to one or more receiving areas of the main body portion 602 of the handpiece assembly 600. As with the cartridge 610, the waste canister 620 can include one or more mating features with the adjacent portion of the handpiece assembly 600. Further, one or more O-rings 624 or other sealing members can be used to prevent or reduce the likelihood of leaks between the waste canister 620 and the main body portion 602 of the handpiece assembly 600.

With continued reference to FIG. 12, the handpiece assembly can include a port 608 or other connection for a power source or other electrical connection. In some embodiments, the port 608 is configured to receive an AC adapter or transformer (e.g., 12 volt charger). In other embodiments, the handpiece assembly 600 comprises a rechargeable battery or other power source (not shown) which may be recharged via the port 608.

Figure 15:
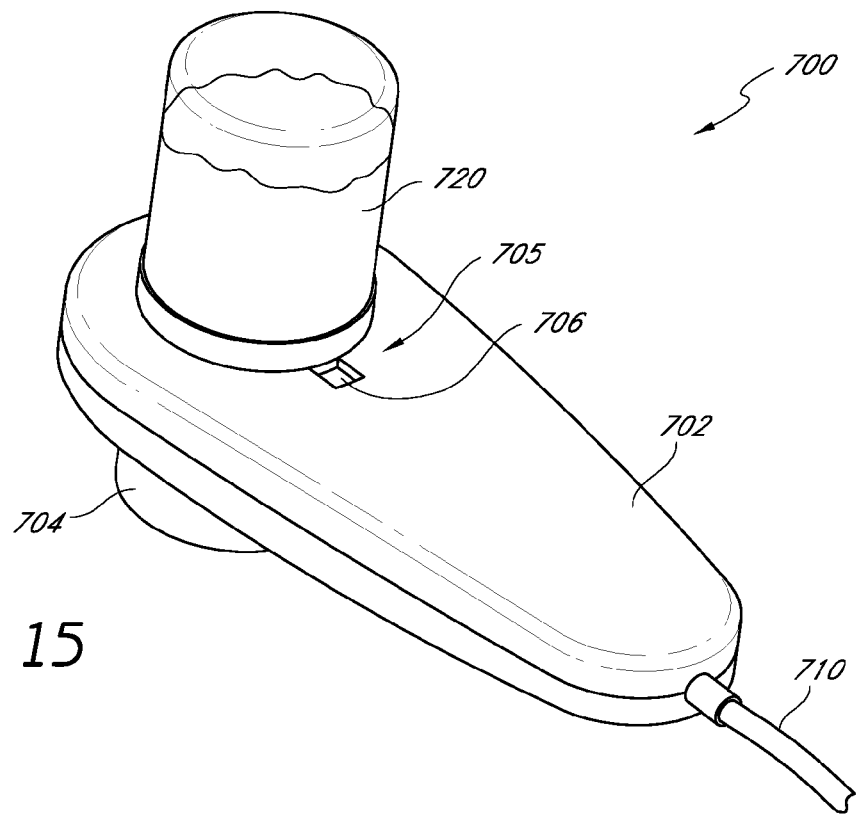
FIG. 15 illustrates a perspective view of a handpiece assembly according to one embodiment.
Figure 16:
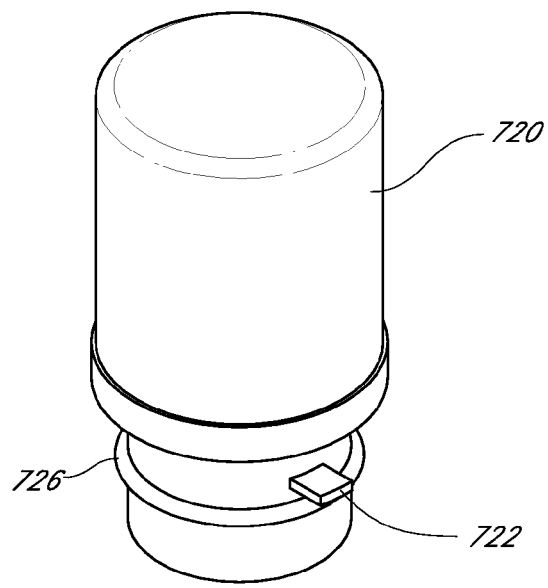
FIG. 16 illustrates a cartridge or other container configured for placement within a corresponding area of the handpiece assembly of FIG. 15.
Figure 17:
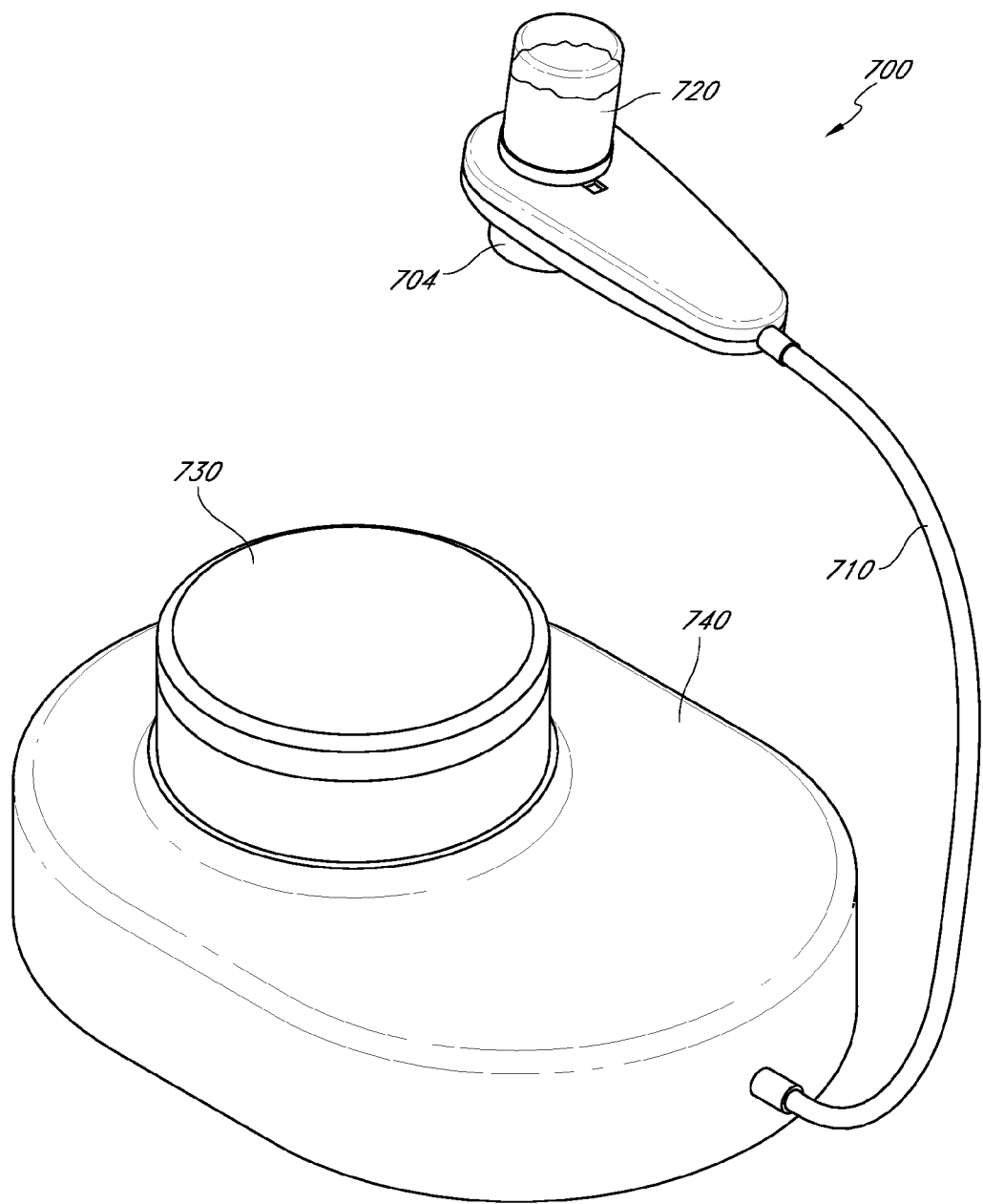
FIG. 17 illustrates a handpiece assembly in fluid communication with a fluid transfer system and a waste canister according to one embodiment.

FIGS. 15-17 illustrate another embodiment of a handpiece assembly 700 that comprises, among other things, a main body portion 702, a working tip 704 and a docking area 705 for receiving a cartridge 720. As shown in FIG. 16, the cartridge 720 can comprise a locking ear 722 or other protruding member that is sized, shaped and otherwise configured to help mate and secure the cartridge 720 to the docking area 705. For example, the docking area 705 can include a recess 706 (e.g., turn lock feature) that is adapted to receive the locking ear 722 or other member of the cartridge 720. Once the cartridge 720 is aligned with and inserted into the recess 706, it can be rotated or otherwise moved to temporarily secure the cartridge 720 to the main body portion 702 of the assembly 700.

When the contents of the cartridge 720 have been emptied and/or when a user wishes to use fluids and/or materials contained with a different cartridge 720, the process by which the cartridge 720 was secured within the docking area 705 can be reversed. For example, the cartridge 720 can be rotated so that the locking ear 722 or other protruding member generally aligns with the recess 706 to permit the cartridge 720 to be removed. As with other embodiments, the illustrated cartridge 720 can include an O-ring 726 or other sealing member to prevent or reduce the likelihood of leaks.

With continued reference to FIGS. 15-17, for aesthetic, ease of handling and/or any other reason, the handpiece assembly 700 can include a tapered shape. As with any other embodiments disclosed herein, or variations thereof, the handpiece assembly 700 can be designed with finger grips or other features that facilitate a user to grip and manipulate the handpiece assembly 700 during use. In addition, the outer surface of any of the embodiments of the handpiece assemblies discussed and/or illustrated herein (or variations thereof) can comprise one or more durable materials that are configured to withstand the elements to which they may be exposed. In some embodiments, the exposed surfaces of a handpiece assembly comprise plastics, metals (e.g., stainless steel) and/or the like.

With continued reference to FIG. 17, the handpiece assembly 700 can be placed in fluid communication with a housing 740 and a waste canister 730 via one or more conduits 710. As shown, the housing 740 can receive a removable waste canister 730 along its upper surface. Alternatively, the housing 740 can be adapted to receive one or more waste canisters 730 at any other portion or location. In some embodiments, the canister 730 can be advantageously removed from the housing 740 for emptying, cleaning and/or any other purpose. As with other embodiments disclosed herein, the housing 740 can comprise an internal and/or external pump or other fluid transfer device. Such a fluid transfer device can be used to remove waste fluids and/or other materials away from the tip 704 of the handpiece assembly 700 (e.g., via a waste conduit 710), and in some arrangements, simultaneously draw treatment serums and other fluids from the canister 720 toward the tip 704 of the handpiece assembly 700.

The pump, other fluid transfer device and/or any other electric component or features of the system can be operated by one or more power sources (e.g., AC, DC, rechargeable or disposable batteries, etc.). In addition, the handpiece assembly 700 and/or the housing 740 can include buttons, dials and/or other members that permit a user to selectively control the operation during a treatment procedure.

Figure 18:
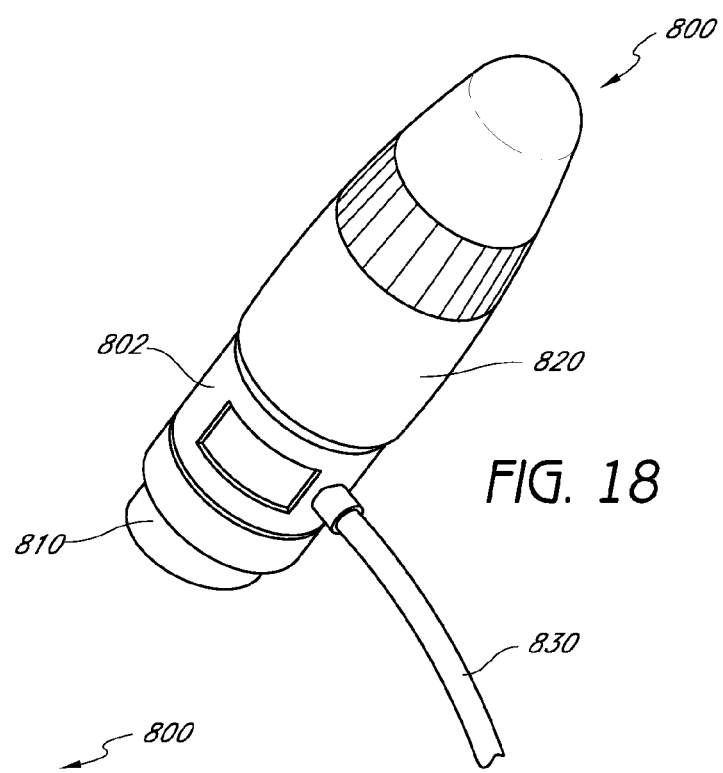
FIGS. 18 and 19 illustrate an embodiment of a handpiece assembly.
Figure 19:
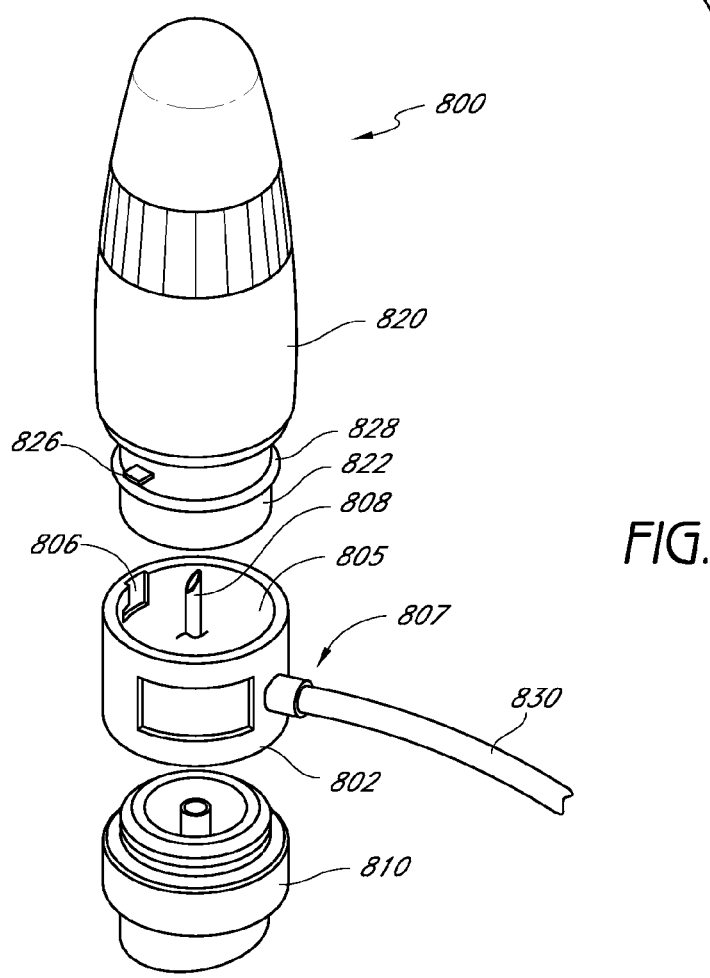

FIGS. 18 and 19 illustrate another embodiment of a handpiece assembly 800 configured for use in a skin treatment system. Like in other embodiments disclosed herein, the depicted handpiece assembly 800 comprises a main body portion 802, a removable tip 810 and a receiving or docking area 805 for securely receiving a cartridge 820. As shown, the main body portion 802 of the handpiece assembly 800 can comprise a port 807 to which a conduit 830 or other channeling member may connect. According to some embodiments, the conduit 830 is placed in fluid communication with a vacuum pump or other fluid transfer device (not shown) for removing waste materials away from the treatment surface (e.g., tip 810).

As discussed herein in reference to other arrangements, the cartridge 820 can include a nozzle portion 822 with a locking ear 826 or other protruding member that is configured to engage and mate with a corresponding slot 806, recess and/or other feature of the docking area 805. Further, the nozzle of the cartridge 820 can include an O-ring 828 or other sealing member to prevent or reduce the likelihood of leaks when fluids and/or other substances are being transferred from the cartridge 820 to the tip 810. In some embodiments, the end of the nozzle portion of the cartridge comprises a membrane or other member (not shown) that can be punctured or otherwise compromised by a hollow tube 808, spike or other member when the cartridge 820 is secured within the docking area 805.

Figure 20A:
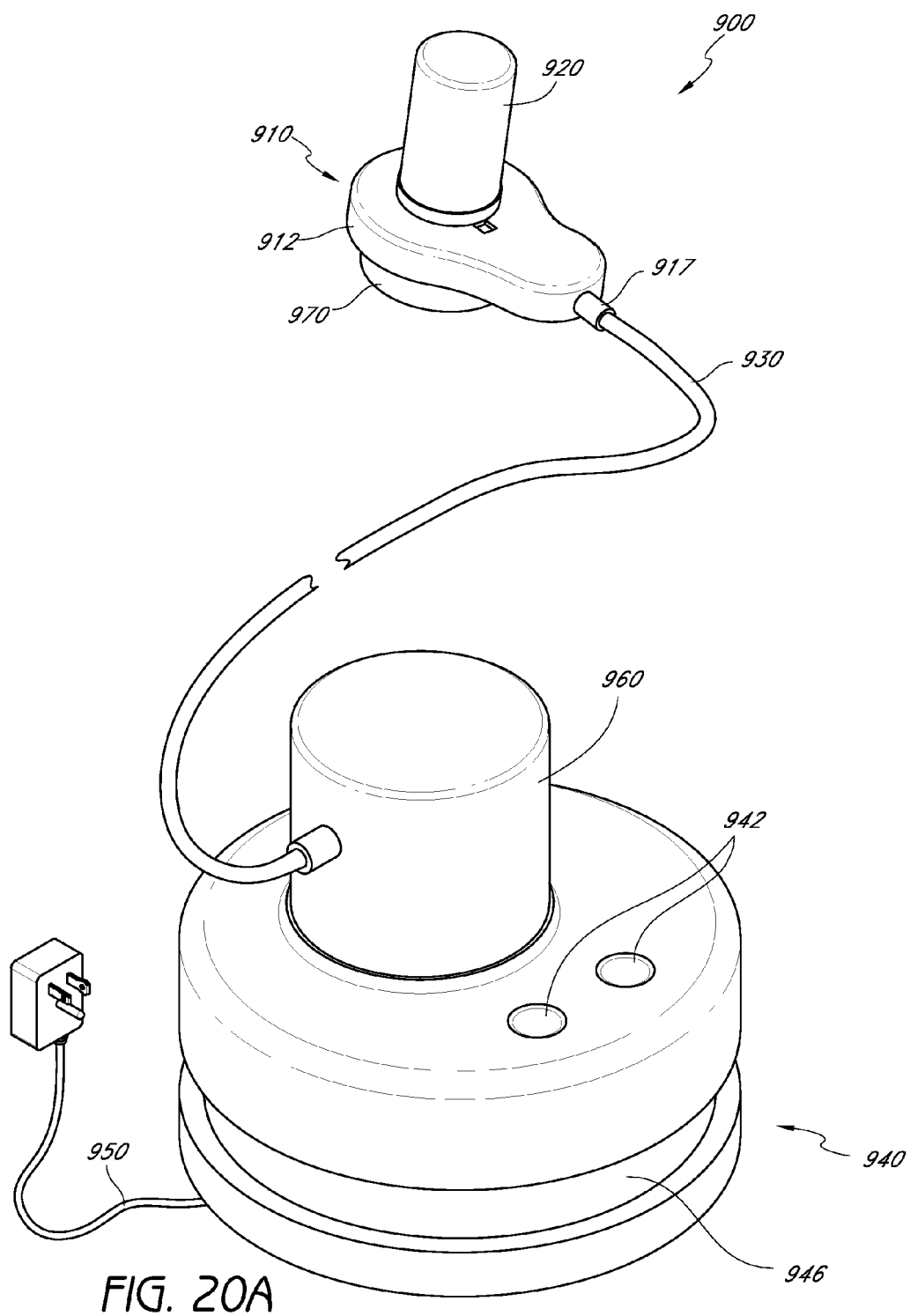
FIG. 20A illustrates a perspective view of a handpiece assembly in fluid communication with a waste canister in accordance with one embodiment.

Another embodiment of a skin treatment system 900 comprising a handpiece assembly 910, a replaceable cartridge 920 and a separate base member 940 is illustrated in FIG. 20A. As shown, the handpiece assembly 910 can comprise a main body portion 912 to which a cartridge 920 and a removable tip 970 can be secured. In addition, the handpiece assembly 910 can include a port 917 that is used to place the handpiece assembly 910 in fluid communication with the base member 940 via one or more conduits 930. As with other embodiments disclosed herein, the cartridge 920 can be selectively secured to and/or removed from the main body portion 912 of the handpiece assembly. Thus, the cartridge 920 can include one or more locking ears, O-rings and/or the like.

In addition, the base member 940 can include a waste canister or container 960 that is adapted to receive waste fluids and other substances. As with the cartridge 920, the waste canister 960 can be configured to be selectively secured to and/or removed from the base member 940 for emptying, cleaning, replacement and/or any other purpose.

Further, in some embodiments, the base member 940 comprises one or more controls (e.g., ON-OFF switches, other switches, knobs and/or the like) for regulating the operation of the system. As shown, a power supply or other electrical connection 950 can be used to power the base member 940, a vacuum pump or other fluid transfer device contained within the base member 940 (or any other portion of the system) and/or any other electrical component or subcomponent of the system. Further, the base member 940 can comprise a recessed area 946 along its lower portion which is configured to receive one or more conduits 930, power cables and/or the like.

Figure 20B:
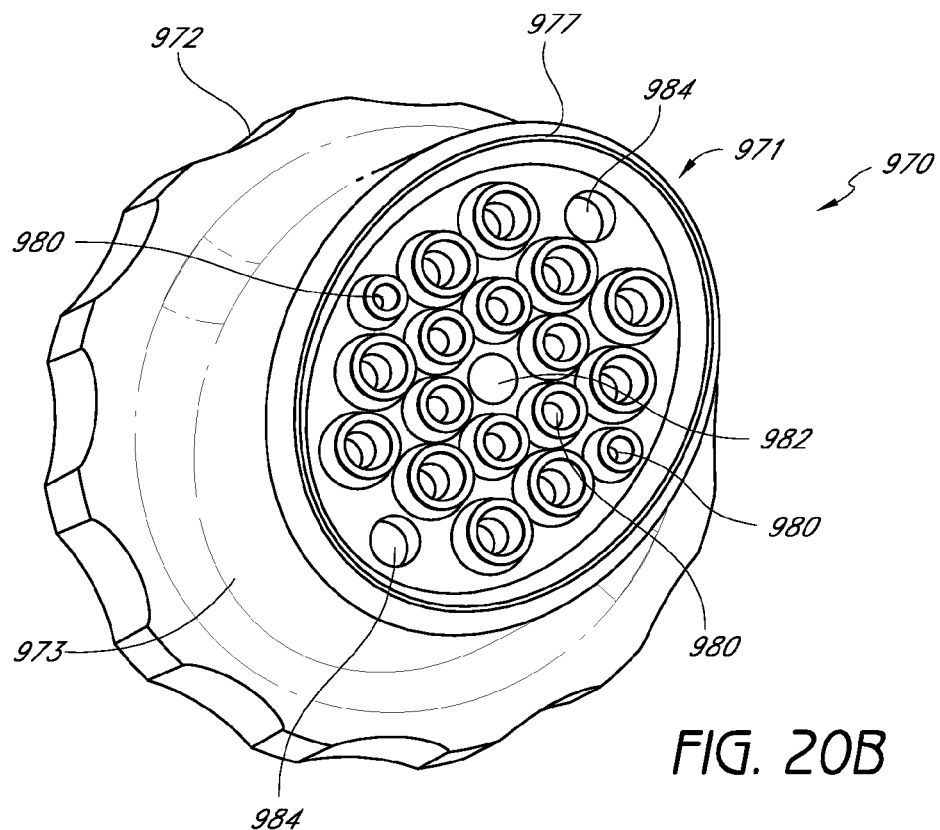
FIG. 20B illustrates a top perspective view of one embodiment of a removable tip adapted for placement on a handpiece assembly.
Figure 20C:
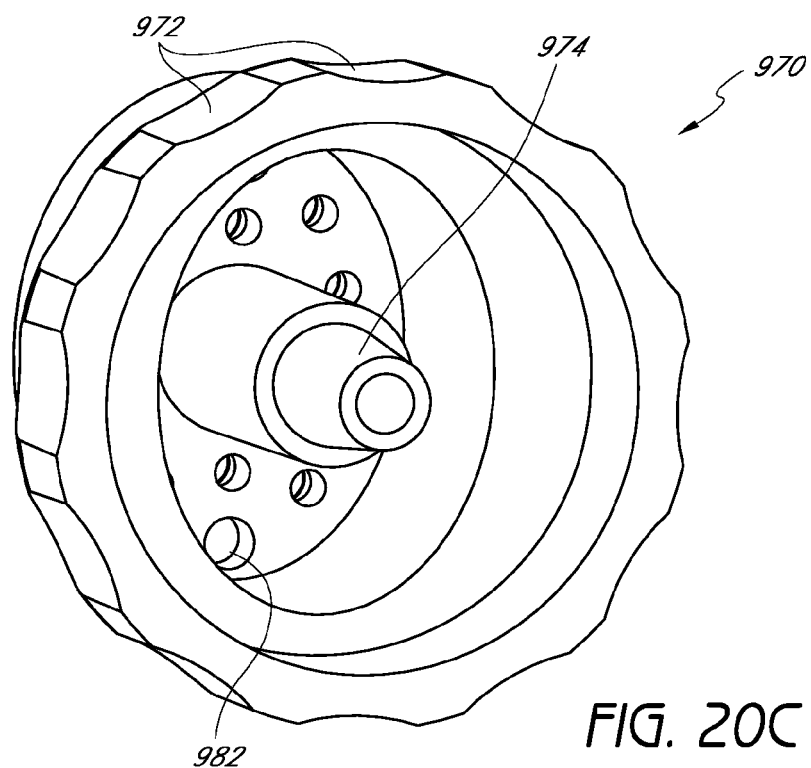
FIG. 20C illustrates a bottom perspective view of the removable tip of FIG. 20B.

FIGS. 20B and 20C illustrate different views of one embodiment of a removable tip 970 configured for placement on a handpiece assembly as disclosed herein. As shown, the tip 970 can include a tip body portion 973 and a tip skirt portion 972 extending along the bottom of the tip body portion 973. The skirt portion 972 can include a plurality of gripping members or other features (e.g., recesses, protrusions, etc.) to facilitate the handling of the tip 970.

A tip can be configured to slidably connect to the distal end and/or any other portion of a handpiece assembly. For example, in some embodiments, the tip can be press fit onto the handpiece assembly. One or more O-rings or other sealing members can be used between adjacent surfaces of the tip and the handpiece assembly to prevent or reduce the likelihood of undesirable leaks. In other embodiments, a tip can be secured to a handpiece assembly using any other method or device, such as, for example, a threaded connection, interlocking tabs, flanges or other members, other fasteners and/or the like. In still other arrangements, the tip can be permanently or semi-permanently attached to the handpiece assembly.

In the embodiment illustrated in FIGS. 20B and 20C, the tip 970 comprises one or more surfaces, elements and/or features along its distal end 971 that are configured to treat (e.g., exfoliate) skin. Such tips can include one or more treatment elements, either in addition to or in lieu of abrasive elements. As used herein, "abrasive element" is a broad term and includes, without limitation, protruding elements, abrasive materials (e.g., grit, sandpaper-like material, other coarse materials, etc.), roughened surfaces, contoured surfaces, surfaces with openings, recesses or other features, brushes, blades, surfaces impregnated with diamonds or other materials and/or the like. Further, as used herein, "treatment element" is a broad term and includes, without limitation, an abrasive element, massage elements or features, elements or features configured to moisturize or apply one or more treatment agents or fluids, polishing or soothing elements or features and/or the like. As discussed, any embodiments of a tip for a handpiece assembly can comprise one or more treatment elements and/or abrasive elements, as desired or required by a particular application.

As illustrated in FIGS. 20A and 20B, the tip 970 can include a lip 977 or other ridge member along its outer periphery. The lip member 977 can generally define the periphery of the distal end 971 of the tip 970. In some embodiments, when the tip 970 is positioned against the skin, the lip member 977 inhibits or substantially inhibits fluids or other materials from escaping a space generally defined between the tip 970 and the adjacent skin surface.

With continued reference to FIGS. 20B and 20C, the tip 970 can include a plurality of protruding members 980 positioned along its distal end 971 and within the interior of the lip member 977. The protruding members 980 can be posts or other cylindrically-shaped objects. In some embodiments, the protruding members 980 comprise relatively sharp edges, which can be configured to remove skin. The protruding members 980 can have relatively sharp planing blades. The plurality of protruding members 980 can ablate or roughen a plurality of smaller sections of the skin being treated.

As illustrated, the outer diameter or other comparable dimension (e.g., length, width, etc.) of the posts or other protruding members 980 can vary. In other arrangements, the diameter and/or other dimensions of the protruding members can be similar or substantiality similar. The posts or other protruding members 980 can be located, spaced and otherwise oriented along the distal end 971 of the tip 970 in any desired or required manner.

It will be appreciated that the size, shape, spacing, orientation, location and/or other properties of the protruding members 980 can be different than illustrated and disclosed herein, as desired or required by a particular procedure or application. As discussed herein, the lip member 977 of the tip 970 can help create an enclosed space generally defined between the distal end 971 of the tip 970 and the skin surface being treated. Therefore, according to some embodiments, the lip member 977 extends above the top of the protruding members 980 so that the protruding members are within the enclosed space during a treatment procedure. In other embodiments, the top surface of the lip 977 is generally aligned with the top surface of or below the protruding members 980.

With reference to FIGS. 20B and 20C, the tip 970 can include an interior delivery stem 974 that is configured to place the distal end 971 of the tip 970 in fluid communication with the one or more delivery channels or other conduits located within the handpiece assembly. For example, the delivery stem 974 can be sized, shaped and otherwise adapted to receive fluids and/or other materials from an internal delivery channel of the handpiece assembly.

As illustrated in FIGS. 20B and 20C, the distal end 971 of the tip 970 can include an opening 982 through which fluids and/or other materials conveyed by the delivery stem 974 may exit. As shown, the opening 982 can be located at or near the center of the distal end 971 of the tip 970. In other arrangements, a tip 970 can include additional stems 974 and/or openings 982. In addition, the size, shape, location and/or other details of the openings 982 can be different than illustrated herein.

Moreover, the distal end 971 of the tip 970 can include one or more outlet openings 984 through which exfoliated skin, spent serums, other waste liquids, fluids and other materials and/or the like can be removed. In the embodiment illustrated in FIGS. 20B and 20C, the tip 970 includes two outlet openings 984. However, more or fewer openings can be included, as desired or required. In addition, some or all of the posts or other protruding members 980 can be generally hollow so that they perform a similar function as other outlet openings 984 of the tip 970. In other embodiments, however, some or all of the protruding members 980 are not hollow or do not include openings therethrough.

In some embodiments, once the distal end 971 of a tip 970 is positioned against the skin being treated, an enclosed space can be created between the skin surface and tip, generally along the interior of a peripheral lip member or other ridge. Therefore, as a vacuum or another suction source is generated in the handpiece assembly, exfoliated skin, spent serum, other fluids and/or other materials can be removed away from the tip 970. At the same time, the delivery stem 974 of the tip 970 and any other conduit or space that is in fluid communication with it may also be subjected to a suction force. Consequently, serums, other fluids and/or other treatment materials can be advantageously transported to the distal end 971 of the tip 970 through one or more openings 982. As discussed, the tip 970 or variations thereof can comprise any combination of treatment elements and/or abrasive elements, as desired or required by a particular application.

Additional details regarding tips for any embodiments of a handpiece assembly disclosed herein can be found in U.S. patent application Ser. No. 11/392,348 (filed on Mar. 29, 2006 and published as U.S. Publication No. 2007/0156124) and U.S. Provisional Patent Application No. 61/024,504 (filed on Jan. 29, 2008), the entireties of both of which are hereby incorporated by reference herein.

Figure 21:
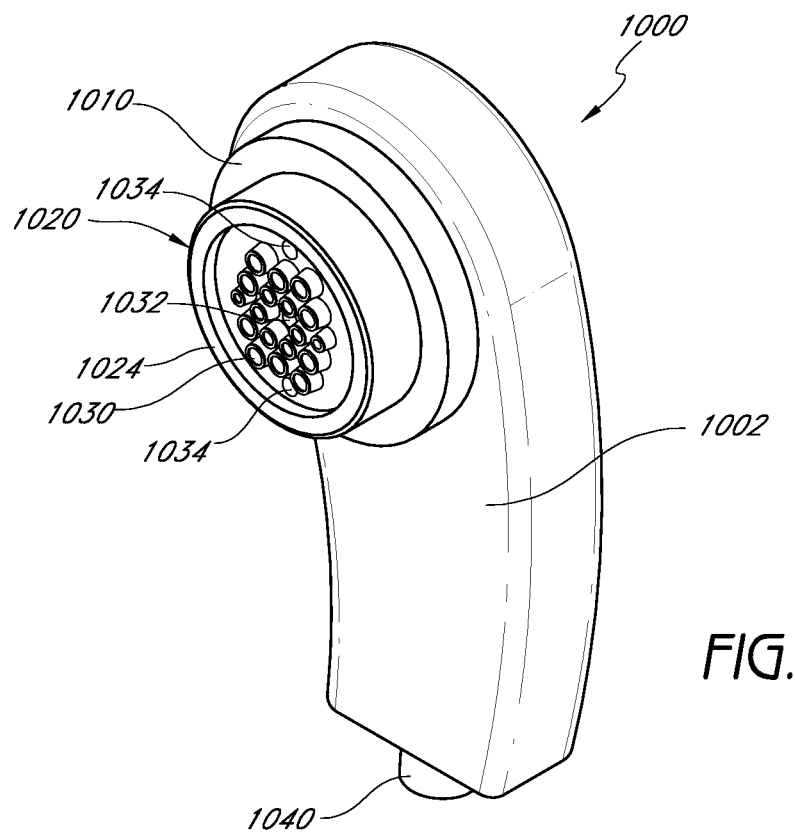
FIG. 21 illustrates a perspective view of another embodiment of a handpiece assembly.

FIG. 21 illustrates another embodiment of a handpiece assembly 1000. In some arrangements, the illustrated assembly 1000 may be particularly well-suited to be used as a shower model. For example, the tip 1020 of the handpiece assembly 1000 can include a dried serum or other material that is configured to dissolve when coming in contact with water and/or other fluids. Thus, once in contact with water, the tip 1020 can be operated to remove skin. For instance, water from a shower head can be used to dissolve the media situated on the tip 1020 of the handpiece assembly 1000. In some embodiments, the handpiece assembly 1000 comprises an internal vacuum pump or other fluid transfer device (not shown) that is used to draw waste liquid and/or materials away from the tip 1020 toward one or more drains 1040. Such drains 1040 may or may not be connected to a separate conduit or other collection device, as required or desired by a particular application.

With continued reference to FIG. 21, the handpiece assembly 1000 can comprise a main body portion 1002 that a user can grasp and manipulate during use. In addition, the tip 1020 can be adapted to be removably positioned onto a raised mounting portion 1010 of the handpiece assembly. In other embodiments, however, the tip 1020 attached directly to the main body portion 1002 of the assembly 1000.

As discussed herein with reference to FIGS. 20B and 20C, the tip 1020 can comprise an outer lip 1024 or other ridge member along its outer periphery. The lip member 1024 can generally define the periphery of the distal end of the tip 1020. In some embodiments, when the tip 1020 is positioned against skin, the lip member 1024 inhibits or substantially inhibits fluids or other materials from escaping a space generally defined between the tip 1020 and the adjacent skin surface. Further, the tip 1020 can include a plurality of protruding members 1030 positioned along its distal end and within the interior of the lip member 1024. As discussed, the protruding members 1030 can be posts or other cylindrically-shaped objects. In some embodiments, the protruding members 1030 comprise relatively sharp edges, which can be configured to remove skin. The protruding members 1030 can have relatively sharp planing blades. Further, the tip 1020 can include one or more openings 1032, 1034 through which treatment fluids, exfoliated skin, other waste materials and/or other substances may enter or exit the working surface of the tip 1020. The size, shape, quantity, location, spacing and/or other details of the openings 1032, 1034 can vary, as desired or required by a particular application or use.

In any of the embodiments disclosed herein, including the one illustrated in FIG. 21, the tip of the handpiece assembly can be configured to rotate, pivot, tilt and/or otherwise move, as desired or required by a particular application.

Figure 22:
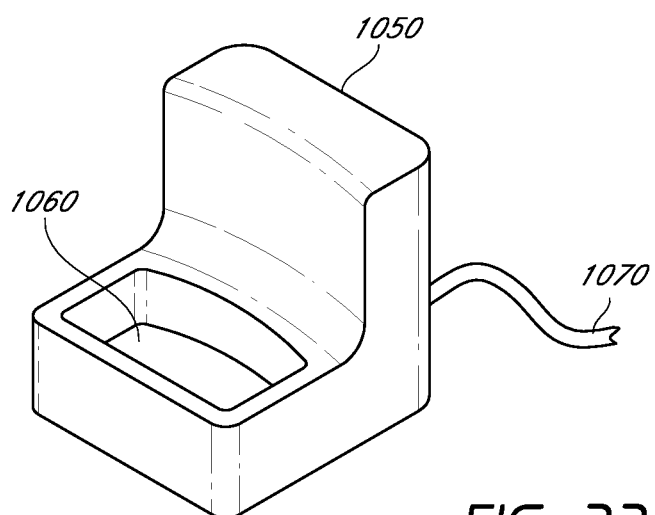
FIG. 22 illustrates a perspective view of a base charging member configured to receive a handpiece assembly according to one embodiment.

FIG. 22 illustrates a charger or docking station 1050 which can be sized, shaped and configured to receive a handpiece assembly. It will be appreciated that any other embodiments of a handpiece assembly disclosed herein can be configured to be placed and stored in such a docking station 1050. The station 1050 can include a cavity 1060 or other receiving area in which one or more portions of a handpiece assembly may be selectively inserted and removed. The station 1050 can be attached to a power cord 1070 or other power source so that a rechargeable battery located within the handpiece assembly can be charged.

Figure 23:
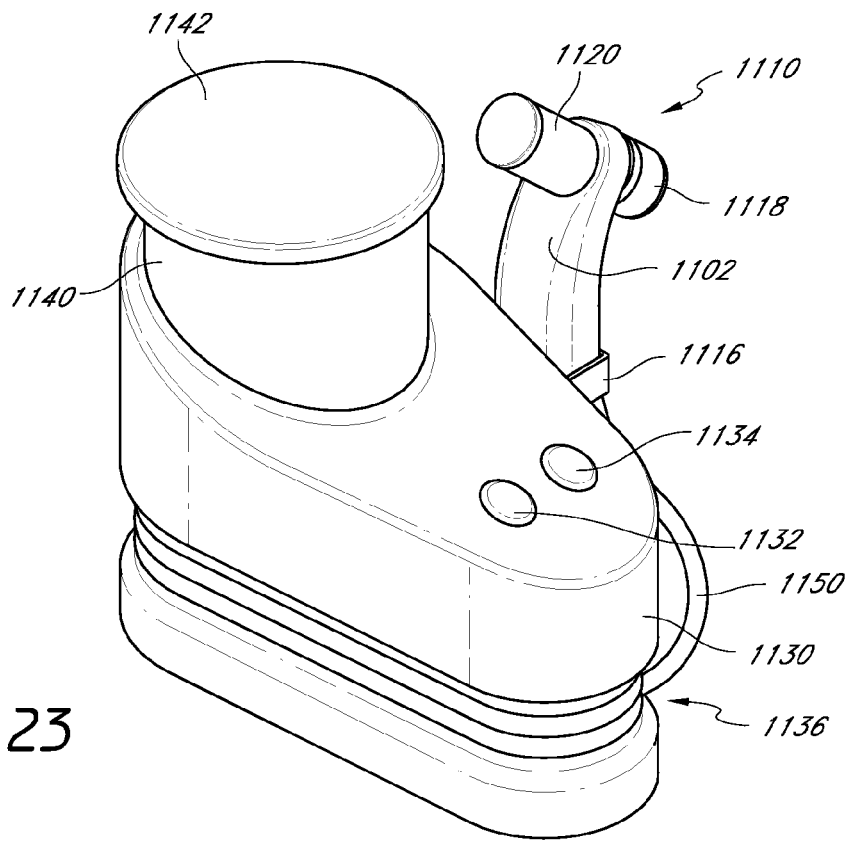
FIG. 23 illustrates a perspective view of a skin treatment system comprising a handpiece assembly and a base member having a waste canister according to one embodiment.
Figure 24:
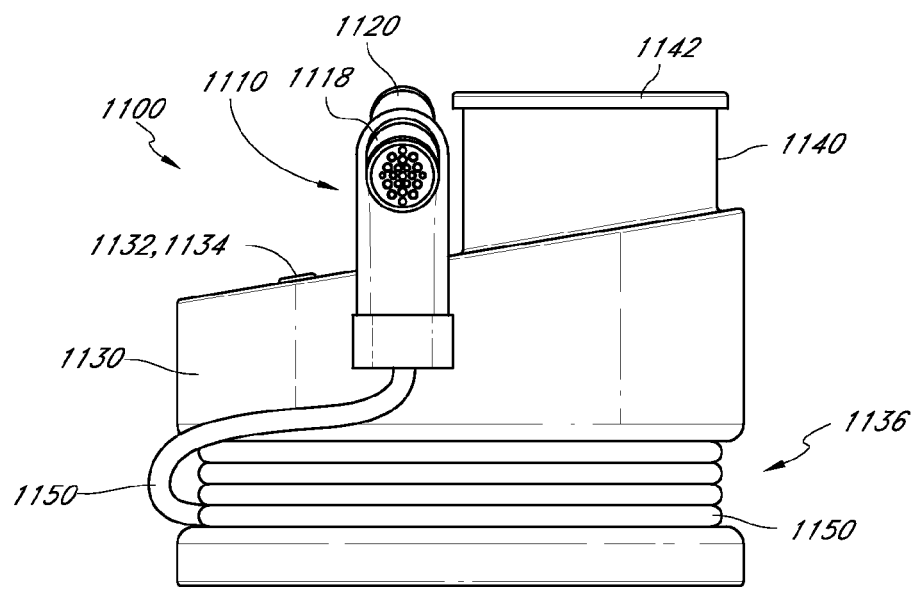
FIG. 24 illustrates a side elevation view of the system of FIG. 23.

Another embodiment of a skin treatment system 1100 comprising a handpiece assembly 1110, a base member 1130 and a waste cartridge 1140 is illustrated in FIGS. 23 and 24. As with other embodiments disclosed herein, the handpiece assembly 1110 can comprise a docking area in which a cartridge 1120 can be selectively removed or attached. In some arrangements, the handpiece assembly 1110 can be secured to a base member 1130 using one or more clips 1116, holders or other members. The handpiece assembly 1110 can be placed in fluid communication with a waste canister 1140 using one or more conduits 1150.

With continued reference to FIGS. 23 and 24, the waste canister 1140 can be configured to be selectively attached to and/or removed from the base member 1130 for emptying, cleaning and/or any other purpose. In some embodiments, the waste canister 1140 comprises a lid 1142 or other cover member. As with any other embodiments disclosed herein, the base member 1130 and/or the handpiece assembly 1110 can comprise one or more buttons 1132, 1134, dials and/or other control members to regulate the operation of the skin treatment system. In addition, the base member can include a recessed region 1136 can enables one or more fluid conduits 1150, power cables or other members to be conveniently coiled therearound. Further, the handpiece assembly 1110 can comprise a main body portion 1102 and a tip 1118 permanently or removably secured thereto.

According to another embodiment, a handpiece assembly can be configured to be used in a shower or in other wet or high moisture conditions. Thus, in some arrangements, the handpiece assembly is waterproof and/or water resistant. In such embodiments, the pump or other fluid transfer device can be driven by electrical power, by water pressure (e.g., one or more connections to running water), by pneumatic power and/or any other method or device. It will be appreciated that such alternative methods or devices of operating a pump or other fluid transfer device can be used with respect to any other embodiment disclosed herein.

Some or all of the embodiments disclosed herein can be particularly useful for less expensive and/or simpler microdermabrasion systems. In some embodiments, such systems can target the home consumer market.

In any of the embodiments described and/or illustrated herein, or variations thereof, treatment fluids and/or other materials can be delivered to the tip of a handpiece assembly using one or more ways. For example, in some embodiments, serums or other substances can be delivered through a supply canister or fluid bottle. Such serums, compositions, other fluids or substances can be pre mixed so that they are delivered to the tip and the skin unmodified or substantially unmodified.

In other embodiments, serums, fluids, gels or other materials can be in the form of a pack container dry granular material, viscous gels and/or the like. Such packs can be mixed with water or some other fluid by a user to a desired concentration. In other embodiments, one or more treatment materials can be impregnated or otherwise embedded into the tips of the handpiece assemblies. Thus, such materials (e.g., powers, solids, gels, etc.) can advantageously dissolve when they contact water, saline or some other liquid. In still other embodiments, the treatment materials can be contained within a capsule, tablet or other enclosure. Such enclosures can be configured to dissolve when placed in water or some other fluid. Therefore, in some embodiments, a user may be required to place a capsule, the contents of a pack or some other materials into a canister and add water or other fluid before use.

In some embodiments, one or more serums or other substances can be delivered to the treatment surface of a handpiece assembly to treat a particular skin condition. For example, the system can be used to treat acne, dry or oily skin, fine lines, sun-damaged skin, other skin diseases or disorders and/or like.

In some embodiments, the serums, other materials and/or a combination of such serums or other materials can be utilized for the treatment of substantially most or all skin types. For example, such serums and/or other materials can be used when the handpiece assembly exfoliates skin.

In another embodiment, the serums, other materials and/ or a combination of such serums or other materials can be used during a follow-up (e.g., secondary, tertiary, etc.) or finish treatment step. For example, such serums and/or other materials can be used to hydrate the skin and/or lighten treat skin damage, either in lieu of or in addition to exfoliating skin. In such embodiments, the serums and/or other materials can comprise anti-oxidants, hyaluronic acid and/or the like.

In yet other embodiments, the serums, other materials and/or a combination of such serums or other materials can be used to target acne or oily skin conditions. It will be appreciated that other serums, other materials and/or combinations of such serums or other materials can be used to target one or more types of skin conditions or treatments. Further, a particular treatment procedure can utilize one, two or more of such serums or other materials during various treatment phases (e.g., exfoliation, finish or polishing treatment, etc.).

In some embodiments, one or more kits can be developed that target a specific type of user, skin condition, desired result and/or the like. For example, such a kit can comprise serums and/or other materials that target teenage acne. As discussed, the serums and/or other materials contained in such kits can be in one or more different forms, such as, for example, liquids, gels, other fluids, powders, solids and/or the like. In some embodiments, such serums and/or other materials can be configured for immediate use. Alternatively, a particular amount of water, saline or other liquids, other dilution or dissolving agents and/or the like may need to be added to the serums and/or other materials to get them to a usable state.

In addition, depending on who the target user is (e.g., teenagers, adults, etc.) and/or how severe a particular condition is, the concentration or strength of the serums and/or other materials can be varied. For example, for younger users, a kit directed at acne treatment can comprise lower concentrations of serums and/or other materials. By way of another example, kits comprising higher concentrations or strengths of serums and/or other materials can be used to treat oily skin or acne in adults. In another embodiment, a kit can be developed to target users whose skin is generally typical (e.g., the users' skin is not abnormally dry or oily, the users do not have excessive amount of acne or scarring, etc.).

As discussed, the kits can include one, two or more different types of treatment combinations. For example, a kit can comprise a first combination of serum(s) and/or other material(s) that is intended to target the exfoliation of skin. The same kit may include a second treatment combination that can be used in a follow-up treatment to treat oily skin or the like. In other embodiments, however, a kit can comprise more or fewer treatment combinations, as desired or required by a particular skin treatment procedure.

The articles, devices, assemblies, systems and/or other items disclosed herein may be formed through any suitable means. The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, it is not intended that the invention be limited, except as by the appended claims.

What is claimed is:

1. A system for treating skin, the system comprising:
a handpiece assembly comprising a tip along a distal end of the handpiece assembly, the tip being configured to contact a skin surface being treated;
a first canister configured to store at least one treatment material, wherein the first canister is configured to removably secure to the handpiece assembly; and
a second canister configured to store waste material removed from tip during use;
wherein an interior of the first canister and an interior of the second canister is each in fluid communication with the tip, so that the at least one treatment material can be selectively delivered from the first canister to the tip, and so that waste material can be selectively delivered from the tip to the second canister during use;
wherein each of the first canister and the second canister is configured to removably and directly secure to the handpiece assembly, such that the handpiece assembly, the first canister and the second canister form a generally unitary structure when the first and second canisters are secured to the handpiece assembly; and
wherein each of the first and second canisters is configured to be removed from and reattached to the handpiece assembly.

2. The system of claim 1, wherein the second canister is configured to be placed in fluid communication with a vacuum or suction source.

3. The system of claim 1, further comprising a fluid transfer device for transferring treatment material from the first canister to the tip, and waste material from the tip to the second canister during use.

4. The system of claim 3, wherein the fluid transfer device comprises a vacuum or suction source that is placed in fluid communication with the tip of handpiece assembly.

5. The system of claim 4, further comprising a power device configured to supply power to the fluid transfer device.

6. The system of claim 5, wherein the power device comprises at least one of a battery or a power source configured to be coupled to a central power supply.

7. The system of claim 1, further comprising at least one conduit configured to place at least one of the first and second canisters in fluid communication with the tip.

8. The system of claim 7, wherein the at least one conduit is positioned, at least in part, within an interior of the handpiece assembly.

9. The system of claim 7, wherein the at least one conduit comprises a first conduit and a second conduit, wherein the first conduit is configured to place the tip in fluid communication with the first canister, and wherein the second conduit is configured to place the tip in fluid communication with the second canister.

10. The system of claim 1, wherein the tip comprises at least one abrasive element, the at least one abrasive element being configured to abrade skin when the tip is moved relative to a skin surface.

11. The system of claim 10, wherein at least one abrasive element comprises at least one of: a protruding element, an abrasive material, a roughened surface, a contoured surface, a surface with at least one opening, a brush, a blade and a surface impregnated with diamonds.

12. The system of claim 1, wherein the tip is removable from the handpiece assembly.

13. The system of claim 1, wherein the tip comprises at least one treatment material positioned along at least one portion of the tip, the at least one treatment material being configured to at least partially dissolve when exposed to water or other liquid.

14. A system for treating skin, the system comprising:
a handpiece assembly comprising a tip along a distal end of the handpiece assembly, the tip being configured to contact a skin surface being treated;
a first canister configured to store at least one treatment material; and
a second canister configured to store waste material removed from tip during use;
wherein an interior of the first canister and an interior of the second canister is each in fluid communication with the tip;
wherein each of the first canister and the second canister is configured to removably and directly secure to the handpiece assembly, such that the handpiece assembly, the first canister and the second canister form a generally unitary structure when the first and second canisters are secured to the handpiece assembly; and
wherein each of the first and second canisters is configured to be removed from and reattached to the handpiece assembly.

15. The system of claim 14, further comprising a fluid transfer device for transferring treatment material from the first canister to the tip, and waste material from the tip to the second canister during use.

16. The system of claim 15, wherein the fluid transfer device comprises a vacuum or suction source that is placed in fluid communication with the tip of handpiece assembly.

17. The system of claim 14, further comprising at least one conduit configured to place at least one of the first and second canisters in fluid communication with the tip.

18. The system of claim 17, wherein the at least one conduit comprises a first conduit and a second conduit, wherein the first conduit is configured to place the tip in fluid communication with the first canister, and wherein the second conduit is configured to place the tip in fluid communication with the second canister.

19. The system of claim 14, wherein the tip comprises at least one abrasive element, the at least one abrasive element being configured to abrade skin when the tip is moved relative to a skin surface.

20. The system of claim 14, wherein the tip comprises at least one treatment material positioned along at least one portion of the tip, the at least one treatment material being configured to at least partially dissolve when exposed to water or other liquid.

* * * * *